United States Patent [19]
Pennybacker et al.

[11] Patent Number: 5,637,110
[45] Date of Patent: Jun. 10, 1997

[54] ELECTROCAUTERY SURGICAL TOOL WITH RELATIVELY PIVOTED TISSUE ENGAGING JAWS

[75] Inventors: William P. Pennybacker, Fremont; Charles L. Nelson, Pleasanton, both of Calif.; Kenneth H. Misser, Redmond, Wash.

[73] Assignee: Stryker Corporation, Kalamazoo, Mich.

[21] Appl. No.: 382,233

[22] Filed: Jan. 31, 1995

[51] Int. Cl.$^6$ .................................................. A61B 17/39
[52] U.S. Cl. ........................... 606/46; 606/49; 606/52; 606/170; 606/206; 606/207
[58] Field of Search ........................ 606/45, 46, 49, 606/51, 52, 170, 206, 207

[56] References Cited

U.S. PATENT DOCUMENTS

| | | |
|---|---|---|
| D. 209,889 | 1/1968 | Shannon et al. . |
| D. 254,090 | 1/1980 | Perry . |
| D. 274,096 | 5/1984 | Shutt . |
| 2,854,005 | 9/1958 | Vido . |
| 3,316,913 | 5/1967 | Swenson . |
| 3,515,139 | 6/1970 | Mallina . |
| 3,894,336 | 7/1975 | Desimone . |
| 3,895,636 | 7/1975 | Schmidt . |
| 4,171,701 | 10/1979 | Walter et al. . |
| 4,226,241 | 10/1980 | Walker, Jr. . |
| 4,572,185 | 2/1986 | Rich . |
| 4,662,374 | 5/1987 | Blake, III . |
| 4,760,848 | 8/1988 | Hasson . |
| 4,872,456 | 10/1989 | Hasson . |
| 4,887,612 | 12/1989 | Esser et al. . |
| 4,896,678 | 1/1990 | Ogawa . |
| 4,945,920 | 8/1990 | Clossick . |
| 4,976,723 | 12/1990 | Schad . |
| 4,985,030 | 1/1991 | Melzer et al. ........................ 606/51 |
| 5,071,430 | 12/1991 | de Salis et al. . |
| 5,082,000 | 1/1992 | Picha et al. . |

(List continued on next page.)

FOREIGN PATENT DOCUMENTS

| | | |
|---|---|---|
| 380 874 | 8/1990 | European Pat. Off. . |
| 484 671 A2 | 5/1992 | European Pat. Off. . |
| 8900376.4 | 4/1989 | Germany . |
| 8903782.0 | 10/1989 | Germany . |

OTHER PUBLICATIONS 2 sketches of straight or curved scissors blades labeled version 5.2 and 5.2.1. (On sale in US before Jan. 31, 1994).

"Endopath Disposable Endoscopic Instruments" by Ethicon (On sale in US before Jan. 31, 1994).

2 sheets—Ancilliary Puncture Forceps and Endoscopic Surgical Forceps, Richard Wolf Medical Instruments Corp. (On sale in US before Jan. 31, 1994).

2 sheets—I.M. Miniatures for the Tight Knee, Meniscal Graspers and Basket Forceps. (On sale in US before Jan. 31, 1994).

3 sheets—Endolaryngeal Micro Surger and Broncho–Esophagoscopic Forceps, Richard Wolf Medical Instruments Corp. (On sale in US before Jan. 31, 1994).

3 sheets—Curved Forceps and O'Connor Hook Punch Forceps by Richard Wolf Medical Instruments Corp. (On sale in US before Jan. 31, 1994).

(List continued on next page.)

*Primary Examiner*—Lee S. Cohen
*Attorney, Agent, or Firm*—Flynn, Thiel, Boutell & Tanis, P.C.

[57] ABSTRACT

A handpowered, low cost, disposable laparoscopic surgical tool has a proximal hand engageable unit, an elongate extension unit and a distal jaw unit. Pulling a trigger of the hand engageable unit forwards an extension rod in the extension unit to pivot the jaws together. In one embodiment of the invention, the handle unit is primarily of molded plastic material for low cost and disposability. In an embodiment, electrocautery contact with the extension unit is through a bendable spring element. In an embodiment specially shaped links and connected jaw portions improve strength and control in opening and closing the jaws.

17 Claims, 17 Drawing Sheets

U.S. PATENT DOCUMENTS

| | | | |
|---|---|---|---|
| 5,133,713 | 7/1992 | Huang et al. | 606/46 |
| 5,133,727 | 7/1992 | Bales et al. | |
| 5,133,735 | 7/1992 | Slater et al. | |
| 5,133,736 | 7/1992 | Bales, Jr. et al. | |
| 5,141,424 | 8/1992 | Christof. | |
| 5,141,519 | 8/1992 | Smith et al. | |
| 5,152,778 | 10/1992 | Bales, Jr. et al. | |
| 5,171,256 | 12/1992 | Smith et al. | |
| 5,171,258 | 12/1992 | Bales et al. | |
| 5,174,300 | 12/1992 | Bales et al. | |
| 5,176,702 | 1/1993 | Bales et al. | |
| 5,192,298 | 3/1993 | Smith et al. | |
| 5,203,785 | 4/1993 | Slater. | |
| 5,258,006 | 11/1993 | Rydell et al. | 606/49 |
| 5,295,956 | 3/1994 | Bales et al. | |
| 5,312,434 | 5/1994 | Crainich | 606/52 |
| 5,314,424 | 5/1994 | Nicholas | 606/52 |
| 5,334,198 | 8/1994 | Hart et al. | 606/52 |
| 5,342,381 | 8/1994 | Tidemand | 606/52 |
| 5,356,408 | 10/1994 | Rydell. | |
| 5,391,166 | 2/1995 | Eggers | 606/207 |
| 5,403,342 | 4/1995 | Tovey et al. | 606/205 |

OTHER PUBLICATIONS

Storz The World of Endoscopy, Proctology, 4th edition Jan. 1991 (On sale in US before Jan. 31, 1994).

2 sheets—Acufex Linear Punch (On sale in US before Jan. 31, 1994).

1 sheet—TMJ Arthroscopy Set brochure, Zimmer Aspen Labs Division. (On sale in US before Jan. 31, 1994).

Storz The World of Endoscopy, Esophagoscopes, 4th edition brochure. (On sale in US before Jan. 31, 1994).

V. Mueller Endoscopy Instruments for Laparoscopic Surgery (On sale in US before Jan. 31, 1994).

Journal of Gynecologic Surgery, vol. 5, No. 2, Summer 1989 Weck, A Squibb Company (On sale in US before Jan. 31 1994).

Sinus Endoscopy from Richards Catalog. (On sale in US before Jan. 31, 1994).

Basket Forceps Features, Baxter Healthcare Corporation Oct. 1, 1990 (On sale in US before Jan. 31, 1994).

Storz The World of Endoscopy, Scissors–Punch–Biopsy Forceps 5th edition Jan. 1992 (On sale in US before Jan. 31, 1994).

1 sheet—Laser Laparoscopic Cholecystectomy Instruments Richard Wolf Medical Instruments Corp. (On sale in US before Jan. 31, 1994).

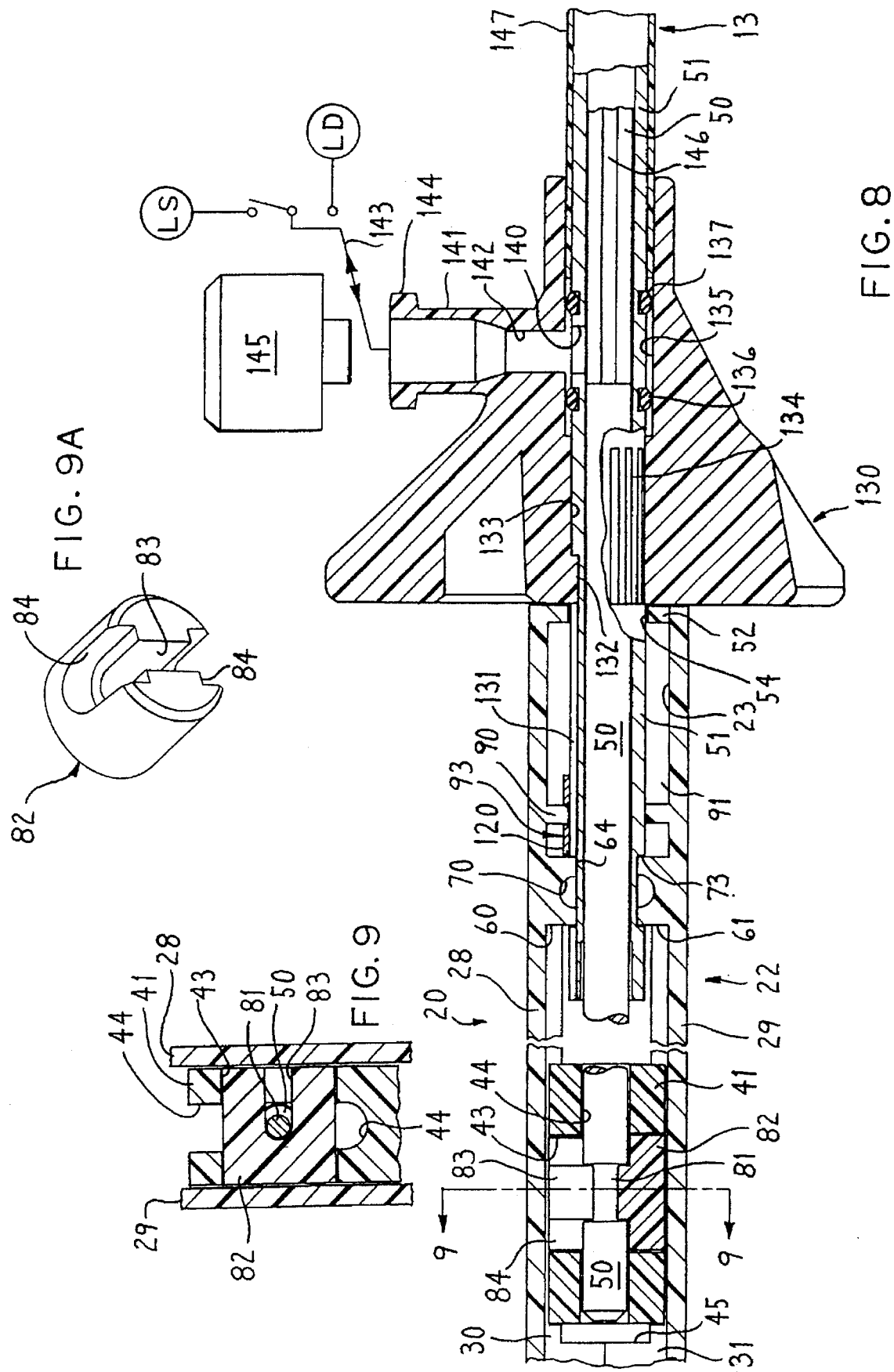

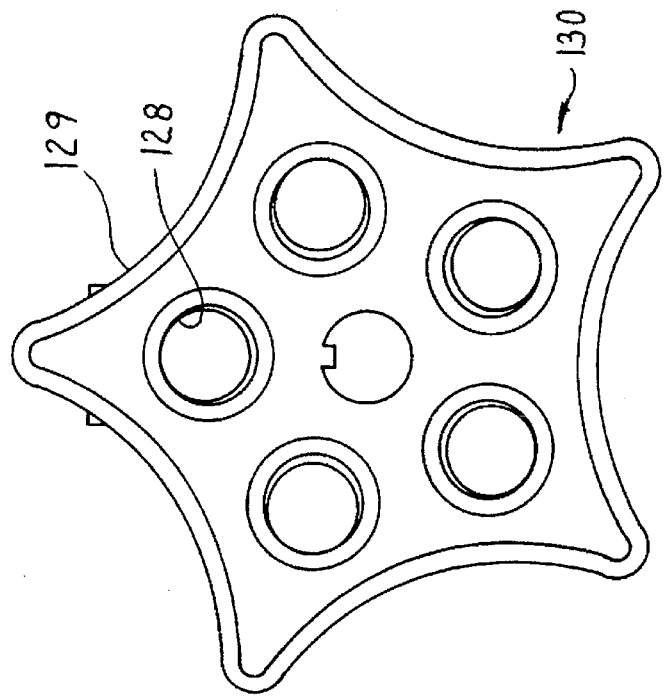
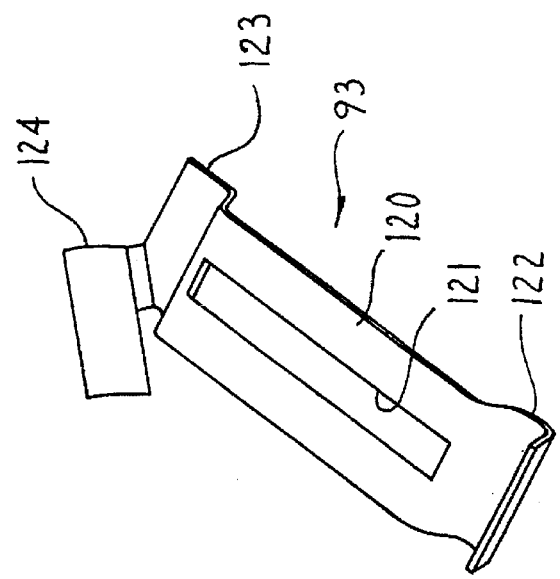
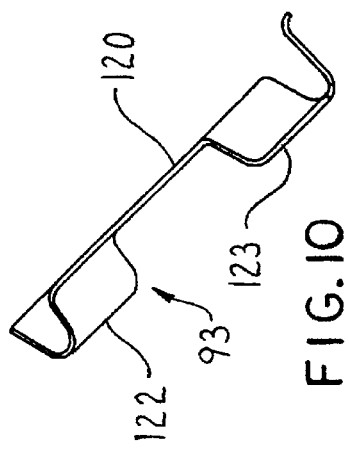

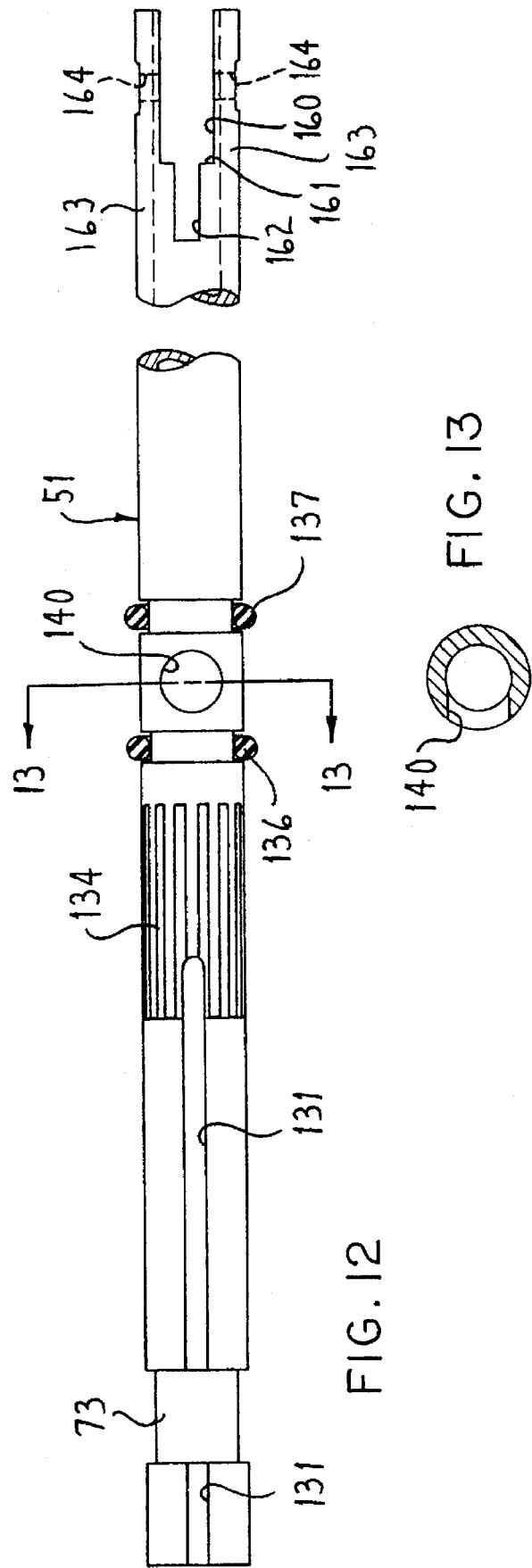

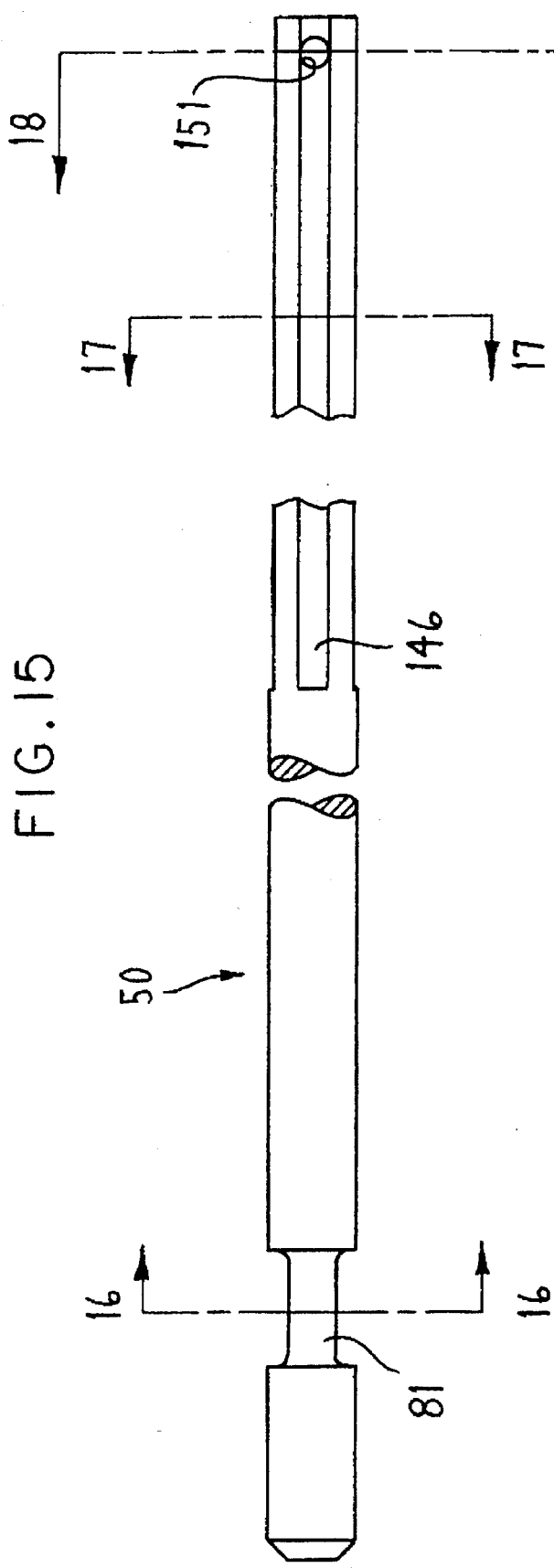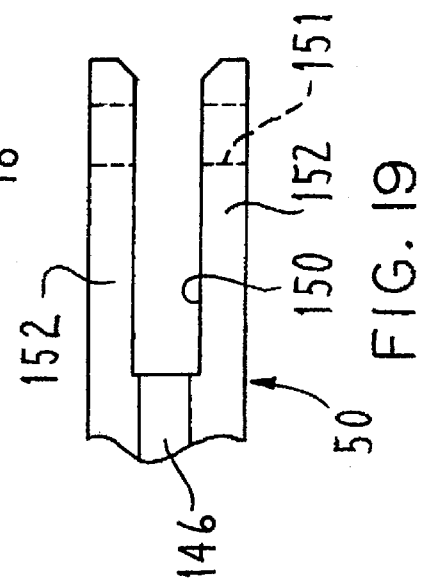

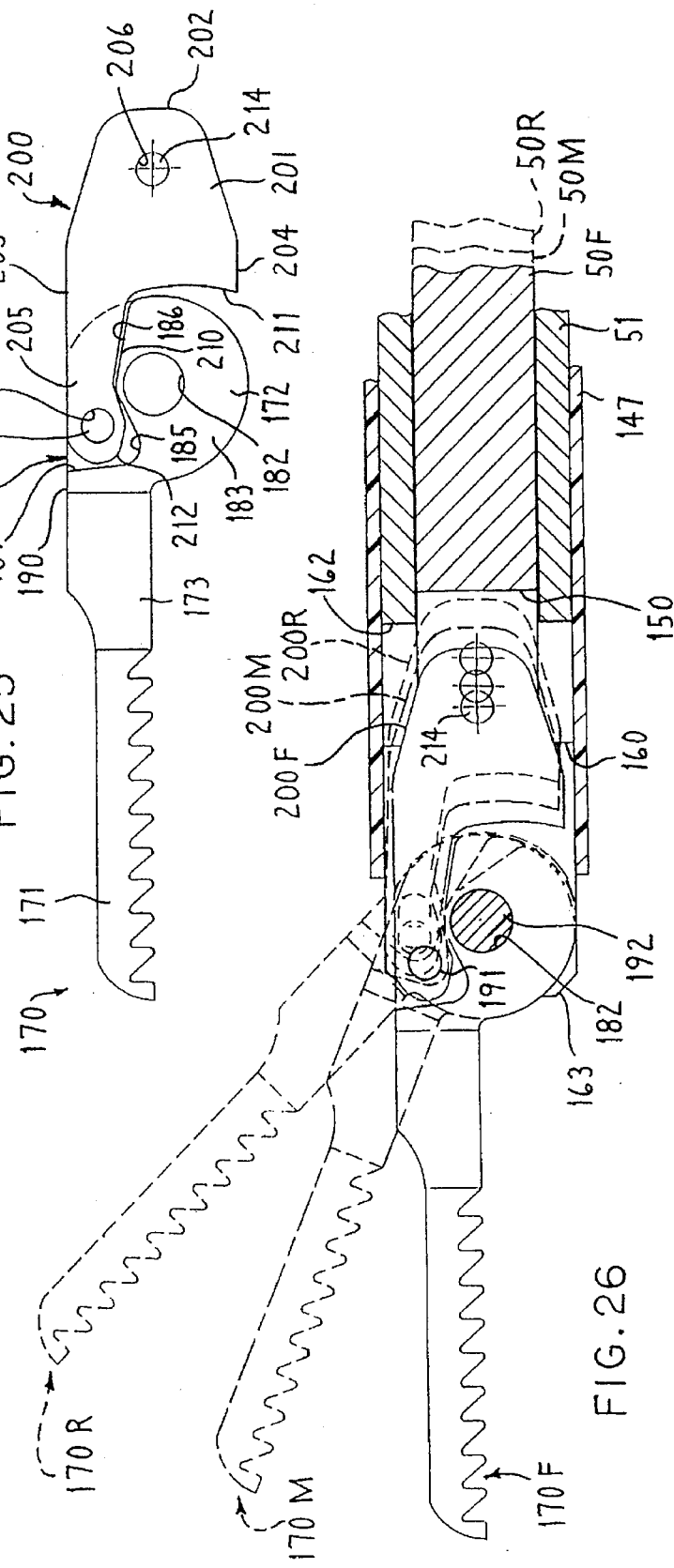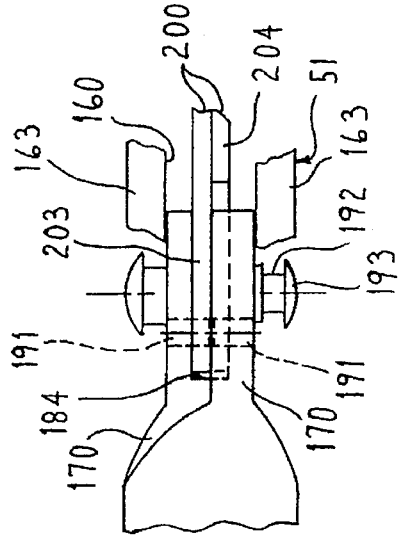

5,637,110

1

ELECTROCAUTERY SURGICAL TOOL WITH RELATIVELY PIVOTED TISSUE ENGAGING JAWS

FIELD OF THE INVENTION

This invention relates to an electrocautery surgical tool having relatively pivoted tissue engaging jaws, such as scissors jaws, dissector jaws and the like.

BACKGROUND OF THE INVENTION

Surgical tools with relatively pivoted tissue engaging jaws, such as scissors-like jaws, and relatively pivoted finger grip handles have been known. For example, Shutt U.S. Design Pat. No. 274,096 shows a device of this general type having an elongate tubular portion interconnecting a proximal hand engageable handle and distal patient tissue engaging jaws. Bales, et al U.S. Pat. No. 5,295,956, particularly in FIGS. 10A–10C shows a surgical scissors device in which a scissors jaws are connected to the proximal pair of finger engageable handles by an elongate tubular extension. As has been common in the past to construct such devices of surgical stainless or the like. Prior devices of that type tend to be complex and hence expensive to manufacture. Such devices, because costly, need to be reusable, and thus must be sterilizable between uses to reduce the risk of cross contamination of successively treated patients.

Accordingly, the objects and purposes of this invention include provision of a surgical tool with relatively pivoted tissue engaging jaws. In one embodiment, the inventive surgical tool is to be constructed with at least a proximal handle structure of moldable plastics material and to be disposable. In one embodiment, the tool is to be capable of electrocautery of tissue, preferably through at least one of the jaws. In at least one embodiment, the tool is to be provided with an electrical connection between an exposed electrocautery terminal connectable to a conventional electrocautery electrical source and conductive, elongate jaw actuating structure extending between the proximal handle structure and a distal jaw. In at least one embodiment, the inventive device includes a simple structure for converting pivoting motion of a hand actuable trigger into reciprocating motion for transfer lengthwise of the tool to pivot a distal jaw. In at least one embodiment of the invention, the distal jaw is rotatable about the length axis of the surgical tool for changing the roll orientation of the jaw with respect to tissue to be worked without need to impart roll motion to the proximal handle. In at least one embodiment, tubular elongate extension unit, interposed between the proximal handle structure and distal jaw, is provided, adjacent the handle, with a hand rotatable wheel carried on the axis of the extension unit and in turn carrying a flushing port suppliable with irrigation liquid or the like transferrable distally therefrom along the tubular extension unit to the distal jaw at a surgical site for applying irrigation liquid to a surgical site. In a preferred embodiment, the tool is configured for laparoscopic surgery wherein a distal jaw unit and tubular extension unit are configured for insertion into the surgical site through a laparoscopic cannula, wherein the jaw unit and tubular extension unit are of minimum diameter so as to minimize the diameter of the laparoscopic cannula required, and wherein the jaw unit in its closed condition is readily insertable through such a laparoscopic cannula and, upon emergence from the distal end of such laparoscopic cannula, into a surgical site, can be actuated to pivotally open a pair of jaws in the jaw unit to a width beyond the outside diameter of the laparoscopic cannula, to engage and work patient tissue at the surgical site.

2

Further objects and purposes of the present invention will be apparent to persons acquainted with apparatus of this general type upon reading the following specification and inspecting the accompanying drawings.

SUMMARY OF THE INVENTION

A handpowered, low cost, disposable laparoscopic surgical tool has a proximal hand engageable unit, an elongate extension unit and a distal jaw unit. Pulling a trigger of the hand engageable unit forwards an extension rod in the extension unit to pivot the jaws together. In one embodiment of the invention, the handle unit is primarily of molded plastic material for low cost and disposability. In an embodiment, electrocautery contact with the extension unit is through a bendable spring element. In an embodiment specially shaped links and connected jaw portions improve strength and control in opening and closing the jaws.

BRIEF DESCRIPTION OF THE DRAWINGS

FIG. 8 is an enlarged cross-sectional view substantially taken on the line 8—8 of FIG. 7.

FIG. 9 is a sectional view substantially taken on the line 9—9 of FIG. 8.

FIG. 9A is a pictorial view of the slotted pin of FIGS. 8 and 9.

FIG. 10 is an elevational view of the spring contact of FIG. 8.

FIG. 11 is a pictorial view of such spring contact.

FIG. 12 is an enlarged fragmentary elevational view of the extension tube of FIG. 8.

FIG. 13 is a sectional view substantially taken on the line 13—13 of FIG. 12.

FIG. 14 is a rear view of the rotator knob 130 of FIG. 8.

FIG. 15 is an enlarged fragmentary view of the actuating rod of FIG. 8.

FIG. 16 is a proximal end view of such rod.

FIG. 17 is a sectional view substantially taken on the line 17—17 of FIG. 15.

FIG. 18 is a sectional view substantially taken on the line 18—18 of FIG. 15.

FIG. 19 is a fragment of the distal end of the FIG. 15 rod taken from above in FIG. 15.

FIG. 25 is an elevational view of a FIG. 20 jaw with its corresponding actuating link.

FIG. 26 is an elevational view taken in central cross-section of the FIG. 20 jaw unit showing the parts in alternative positions.

FIG. 27 is a reduced size fragmentary top view taken substantially from the top of FIG. 22 and showing the relationship of jaws, link and extension tube and their assembled side-by-side relation.

DETAILED DESCRIPTION

Figure 1:
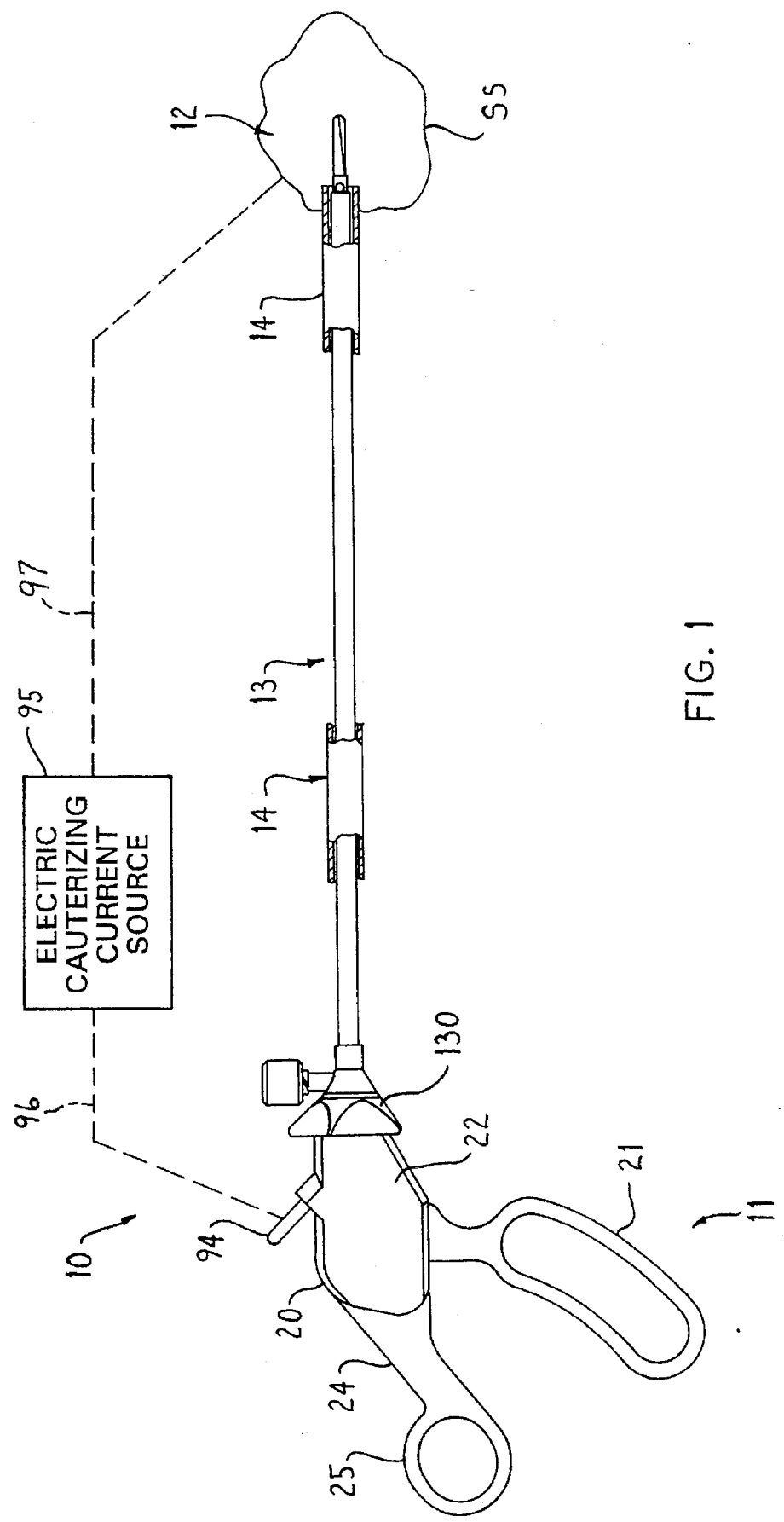
FIG. 1 is a partly schematic elevational view of a tool embodying the invention.

A laparoscopic surgical tool 10 (FIG. 1) embodying the invention comprises a proximal handle unit 11 hand engageable by a surgeon for laparoscopic surgery, a distal jaw unit 12 insertable into a surgical site SS for working of tissue of a patient undergoing laparoscopic surgery, and an intervening elongate extension unit for supporting and actuating the jaw unit upon manipulation of the handle unit. The jaw unit 12 and extension unit 13 are diametrally compactly sized to allow insertion into a conventional laparoscopic cannula, a fragment of which is indicated at 14 in FIG. 1 by way of example. The cannula 14 guides entry of the jaw unit 12 into the surgical site SS, for surgical working of tissue therein. The extension unit 13 thus serves both to support and actuate the jaw unit 12.

The handle unit 11 (FIG. 2) comprises a body 20, a trigger 21 and a cover 22. The body 20 and cover 22 are opposed, shallow, generally cup-shaped elements which when fixed together, as generally indicated in FIG. 1, form a chamber 23 (FIG. 2) for enclosing additional parts of the tool, including the top of the trigger 21. Integrally fixed to and angling rearward and downward from the body 20 is an extension bar 24 (FIG. 2) terminating in a thumb ring 25 engageable by the thumb of the user.

Such body, extension bar, thumb ring, trigger, and cover are preferably of suitable rigid molded plastic material.

Figure 3:
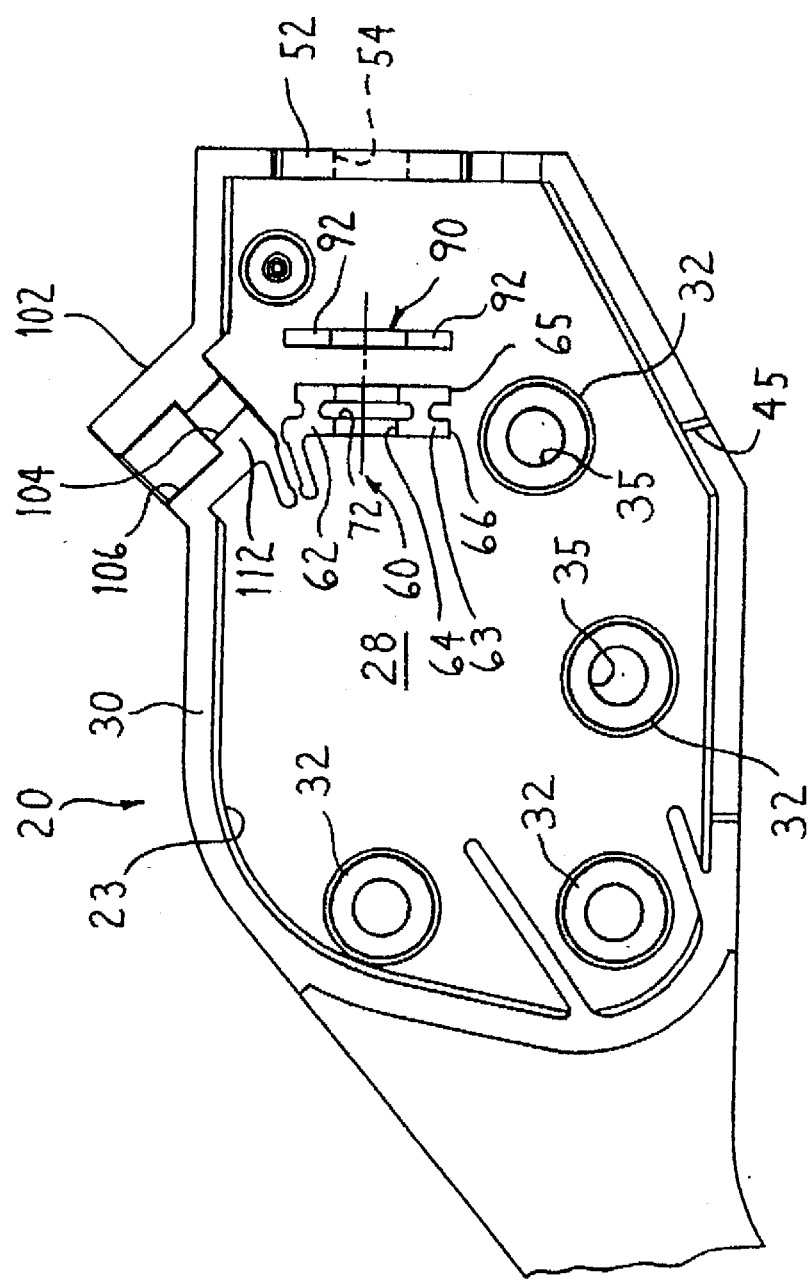
FIG. 3 is an enlarged fragmentary elevational view of the handle unit body of FIG. 1.
Figure 4:
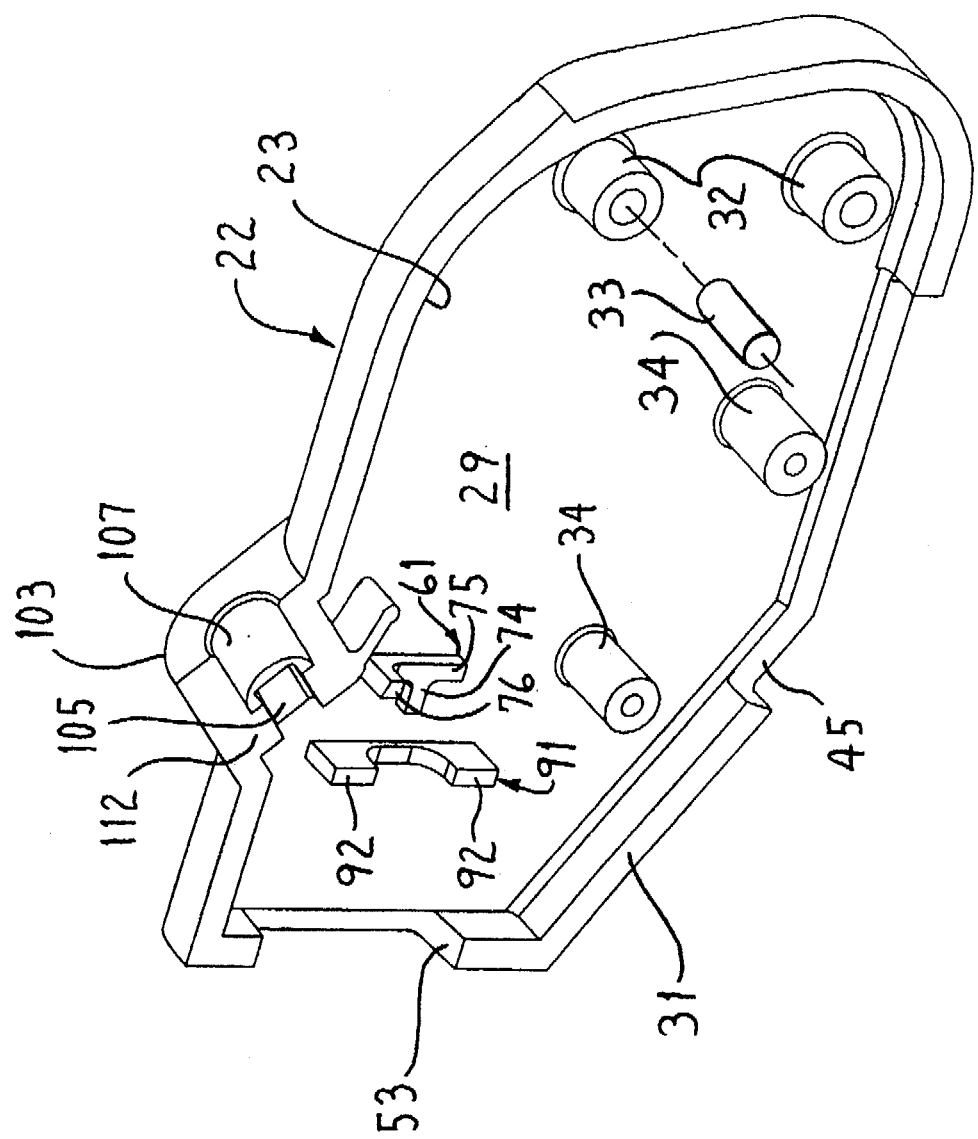
FIG. 4 is an enlarged pictorial view of the handle unit cover of FIG. 1.

The body 20 and cover 22 have opposed parallel side walls 28 and 29 respectively, from the perimeters of which perimeter rims 30 and 31 respectively extend toward each other as generally indicated FIGS. 3 and 4. The perimeter rims 30 and 31 on the body 20 and cover 22 abut, with the cover assembled on the body as shown in FIGS. 1 and 8, to enclose the chamber 23. The body 20 and cover 22 may be located in accurate registry and held together by any convenient means. In the embodiment shown in FIGS. 3 and 4, for example, opposed, hollow, generally cylindrical bosses 32 extend laterally toward each other and may be fixed coaxially together, as by sizing coaxially aligned bosses 32 to telescope one into the other, or as by sizing coaxially opposed hollow bosses 32 to receive a common coaxial connector pin, as at 33 in FIG. 4. It will be understood that the bosses 32 appearing in the present drawings are not to scale. The cover 22 is intended to be permanently affixed to the body 20 in a last stage of assembly of the tool 10, as by the use of adhesive bonding, solvent bonding, localized heat (e.g. laser) bonding, or the like, around the perimeter of the rims 30 and 31, or by friction fit of laterally opposed bosses 32 with respect to each other, or the like.

Figure 5:
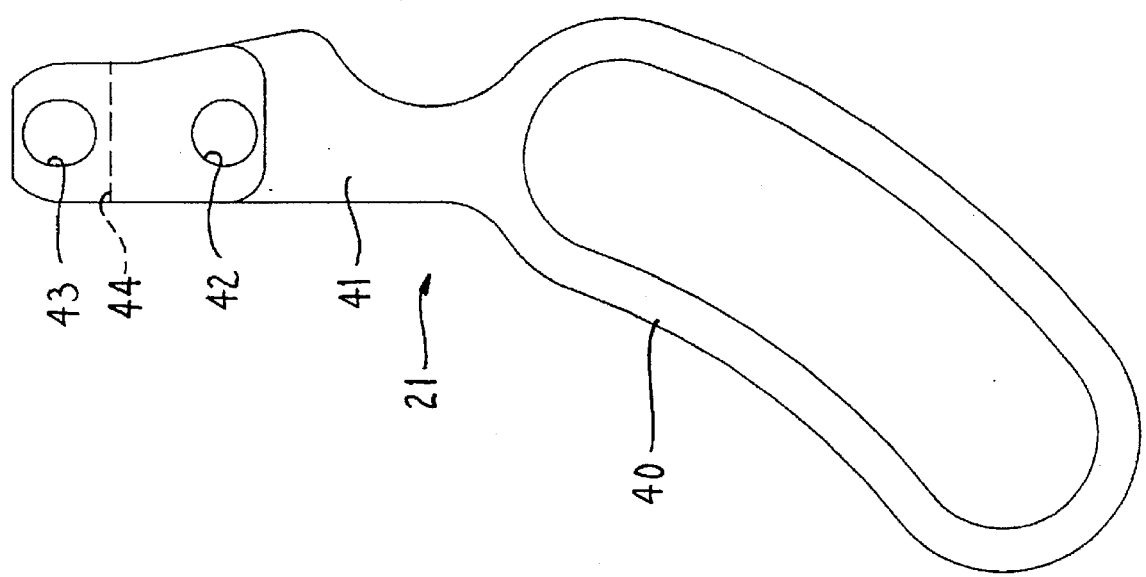
FIG. 5 is an enlarged elevational view of the trigger of FIG. 1.

The trigger 21 (FIGS. 2 and 5) comprises a depending multiple finger loop 40 surmounted by an upstanding arm 41. The arm 41 has a trigger pivot hole 42 intermediate its ends and a drive hole 43 adjacent the top of the arm 41 and spaced above the trigger pivot hole 42. Both holes extend through the arm in a direction perpendicular to the plane of the arm, and hence to the plane of the page in FIG. 5. The drive hole 43 is elongated vertically so as to be oval in shape. A central slot 44 (FIG. 2) in the top of the arm 41 extends forwardly/rearwardly therethrough and opens upward therefrom. The bottom of the slot is below the bottom of the hole 43.

Figure 7:
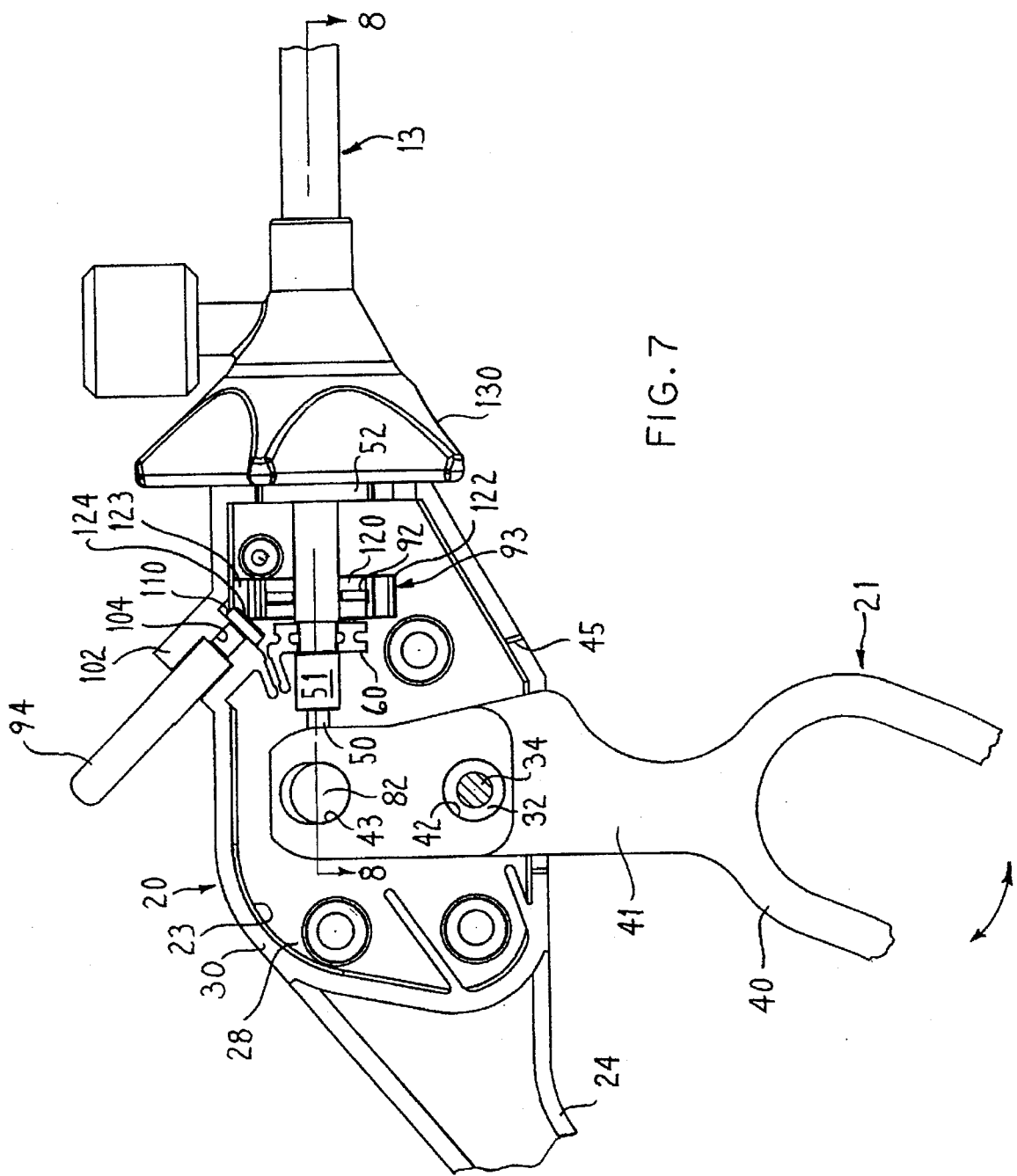
FIG. 7 is a fragmentary elevational view of the FIG. 6 body with additional structure installed.

The bottom portion of the rims 30 and 31 of the body 20 and cover 22 are notched in opposition to each other to thereby form a downward opening window 45, upward through which the arm 41 of the trigger 21 is received into the chamber 23 enclosed by the body 20 and cover 22, as seen in FIG. 7. There the trigger 21 is pivotally supported, for movement in the plane of the paper (and hence parallel to the planes of the body 20 and cover 22) by pivotal insertion of the lower central boss 32 of the body 20 through the trigger pivot hole 42, such that rearward displacement of the depending finger loop 40 of the trigger 21 pivots forward the upper end of the arm 41, including the drive hole 43 therein, for purposes of appearing hereinafter.

The elongate extension unit 13 comprises an elongate axially shiftable actuation rod 50 snugly but axially slidably housed in an elongate extension tube 51 (FIG. 10). It will be understood that the tool 10 is relatively small. For example in one unit constructed according to the invention, the outside diameter of the extension tube 51 is somewhat less than 0.190 inch.

Figure 6:
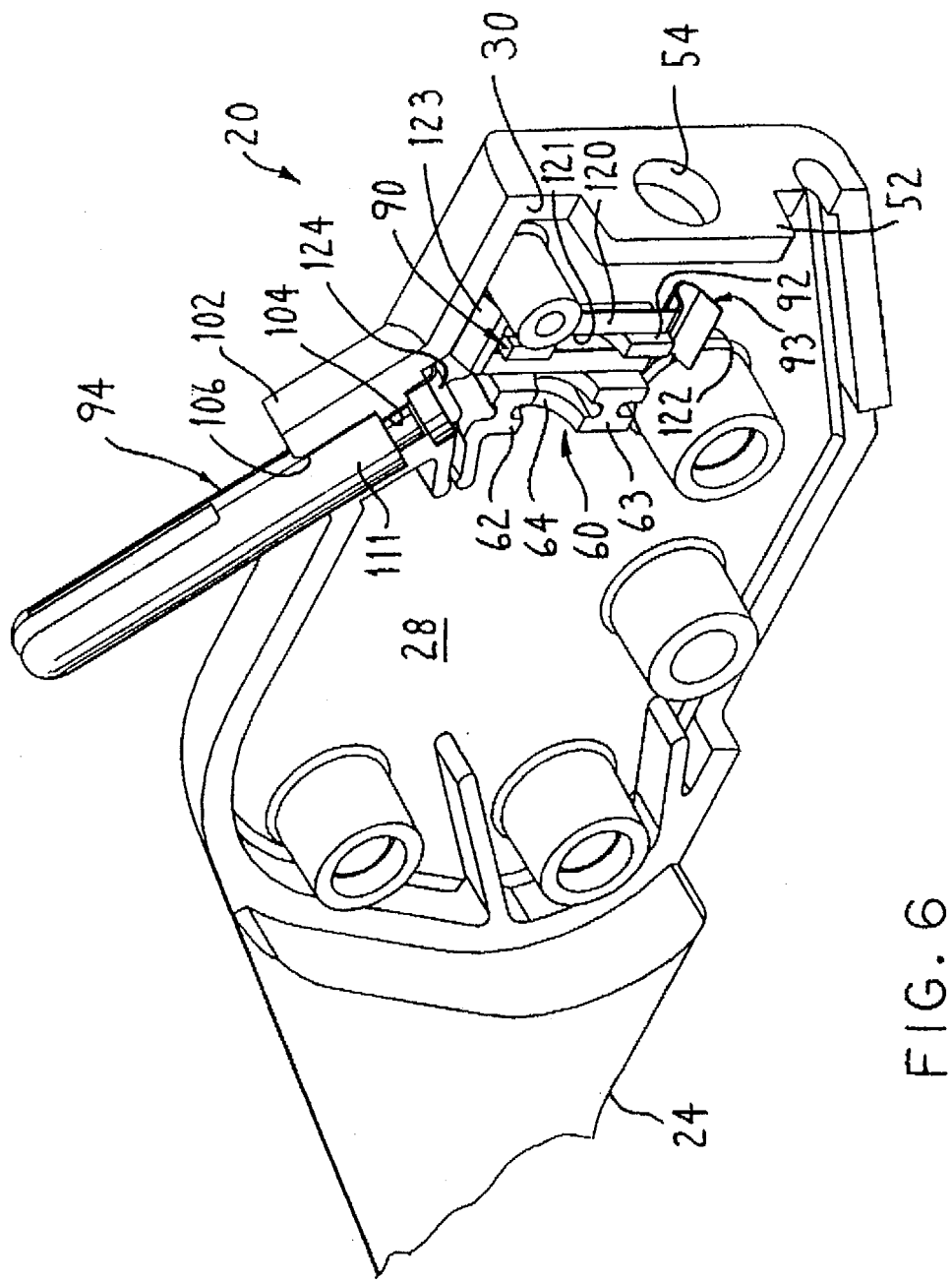
FIG. 6 is an enlarged pictorial view showing a fragment of the body of the handle unit.

The elongate extension unit 13 rotatably mounts on front and rear bearings in the handle unit 11. The perimeter rim 30 at the forward (rightward in FIG. 2) end of the body 20 protrudes laterally toward the cover 22 to form a lateral tab 52 (FIG. 6). The tab 52 fits snugly into a corresponding notch 53 (FIG. 4) in the forwardmost reach of the perimeter rim 31 of the cover 22. A bearing hole 54 (FIG. 6) extends forward through the tab 52 and acts as a front bearing for snugly and rotatably supporting a portion of the extension tube 51, as generally shown in FIGS. 7 and 8. In the preferred embodiment shown, the plane of abutment of the perimeter rims 30 and 31 of the body 20 and cover 22 contains the center of the hole 54 and the central axis of the elongate extension unit 13.

The rear bearing for the extension tube is spaced rearward (leftward in FIG. 3) from, and is coaxially along with, the front bearing hole 54 in the tab 52 (FIG. 6). In the preferred embodiment shown, such rear bearing is formed by laterally opposing rear bearing parts 60 and 61 fixed to and extending laterally inboard from the inner surfaces of the side walls 28 and 29, respectively, of the body 20 and cover 22 respectively. In the preferred embodiment shown, such bearing parts 60 and 61 are integrally molded into the body 20 and cover 22 respectively. The rear bearing 60, 61 is here disposed approximately above the forward end of the downwardly opening trigger window 45. The rear bearing part 60 on the body side wall 28 (FIGS. 3 and 6) is, as seen from the front as in FIG. 6, generally U-shaped, having top and bottom legs 62 and 63 protruding toward the cover 22 and flanking a hemi-circular (here semi-circular) bearing groove 64. In the embodiment shown, the shaped rear bearing part 60 is relatively thick in the front/rear direction (from left to right in FIG. 6) and is divided into front and rear bearing webs 65 and 66 by top, middle and bottom relief slots 70 extending laterally from the side wall 28 of the housing 20 toward the opposing cover 22. The top, middle and bottom relief slots 70 prevent distortion of the axially relatively thick rear bearing part 60 during molding, where the body 20 is of molded plastics material.

The rear portion of the extension tube 51 (FIGS. 2 and 7) has an annular groove 73, preferably of rectangular cross section, which snugly but rotatably fits, both radially and axially, in the semi-circular bearing groove 64 in the rear bearing part 60. The generally U-shaped rear bearing part 60 thus is the axial thrust bearing for the extension tube 51. The rear bearing part 60 also constrains the rear portion of the extension tube against movement upward or downward and toward the housing side wall 28.

The rear bearing part 61 of the cover 22, in the assembled apparatus, engages the annular groove 73 in the extension tube 51 and prevents it from moving sideways (radially) out of the annular groove 73. Thus, the rear bearing 60, 61 acts as a radial thrust bearing to maintain coaxial location of the extension tube 51 while permitting its rotation about its own length axis.

In the embodiment shown, the rear bearing part 61, as seen in FIG. 4, comprises a substantially T-shaped, pad-like protrusion (hereafter T-shaped pad) fixedly extending inward laterally from the side wall 29 of the cover 22. The T-shaped pad has a forward extending leg 74 and a vertically extending crosshead 75 at the rear end of the leg. The crosshead 75 rearwardly opposes the rear bearing web 66 of the 20 and the leg 74 extends forward to substantially the front end of the front bearing web 65, such that the leg 74 and the central portion of the crosshead 75 radially engage in the annular groove of the extension tube 51 in a radial thrust bearing manner, as well as assisting the rear bearing web 66 of the housing 20 in axially locating the extension tube 51, while supporting same for rotation.

The rear bearing part 61 of the cover 22 further includes a finger 76 (FIG. 4) integrally fixed thereon and aimed laterally away from the cover side wall 29 toward the top portion of the rear bearing web 66 of the body, to assist same in preventing upward displacement of the rear portion of the extension tube 51, particularly as the upper part of the trigger arm 41 pivots upward into the central portion of its swing hereafter discussed.

In this way, the proximal end portion of the extension tube 51 is held fixedly but rotatably about its own axis within the chamber 23.

Spaced just forward of the rear bearing 60, 61 and protruding laterally in from the side walls 28 and 29 of the housing 20 and cover 22, are vertically extended, plate-like, laterally opposed, generally U-shaped saddles 90 and 91 (FIGS. 3, 4 and 6). The saddles 90 and 91, like the rear bearing parts 60 and 61 are very closely laterally opposed to each other but need not meet when the cover 22 is assembled on the housing 20. The laterally depressed central portions of the saddles 90 and 91 are sized to allow close passage therethrough of the rotatable extension tube 51 just forward of the annular locating groove 73 therein. The saddle 90 on the side wall 28 of the body 20 carries and locates a spring-like, electrically conductive metal contact 93 hereafter discussed in respect to FIGS. 6, 10 and 11. The U-shaped saddles 90 and 91 have a depressed central portion flanked by top and bottom horns 92 which protrude away from the respective side walls 28 and 29 of the body 20 and cover 22 respectively.

The actuating rod 50, which is axially slidable within the extension tube 51 has a rear end portion extending rearwardly from the extension tube 51 and into the upward opening central slot 44 (FIG. 8) in the arm 41 of the trigger 21 and across the drive hole 43 therein. A slotted drive pin 82 extends axially through the drive hole 43 and is rotatable therein. An annular groove 81 coaxial in the actuating rod 50 coacts with the slotted drive pin 82 (FIGS. 2, 7 and 8) for connecting the top portion of the arm 41 of the trigger 21 to the rear end portion of the actuating rod 50 for forwarding of the actuating rod 50 along the extension tube 51 in response to a rearward pull on the depending finger loop 40 of the trigger 21 by the user of the tool 10.

To this end, the drive pin 82 comprises a member, preferably of molded rigid plastics material, having a generally U-shaped diametrally extending notch 83 opening through one end thereof and sized to snugly but slidably receive diametrally therethrough the annularly grooved portion 81 of the actuating rod 50 (FIG. 8). The notch 83 is flanked at its diametrally opposite ends by diametrally opening generally U-shaped recesses 84 (FIGS. 8 and 9A) for receiving portions of the actuating rod 50 at the opposite ends of the annular recess 81. The axial length of the annular recess 81 is equal to or slightly larger than the diametral extent of the notch 83 and the diameter of the pin 82 is equal to or only slightly less than the minimum diameter of the hole 43, such that clockwise (FIG. 7) pivoting of the trigger 21 positively and axially shifts forward the actuating rod 50.

As the trigger 21 (FIG. 7) is pivoted about its boss 32, its drive hole 43 moves through an arc whose major component of direction is parallel to the direction in which the actuating rod is constrained to move, i.e., along the length axis of the extension tube 51. However, the trigger and drive hole 43 are also a minor component of direction perpendicular to the length axis of the extension tube and hence to the direction of movement available to the actuating rod 50. Accordingly, the elongation of the drive hole 43 in the latter direction allows the drive pin 82 lost motion along the length of the oblong drive hole 43 in the upper end of the arm 41, so that the drive pin 82 does not tend to bend the actuating rod 50 as the drive pin pushes forward or pulls rearward the actuating rod during pivoting at the trigger 40.

As seen in FIG. 8, the drive pin 82 is snugly trapped between the side walls 28 and 29 of the body 20 and cover 22 in the assembled condition of the tool 10. The drive pin 82 thereby cannot escape from the upstanding arm 41 of the trigger 21 and the rear end portion of the actuating rod 50, and must thus accomplish forward and rearward movement of the actuating rod 50 in response to manual rearward and forward pivoting of the finger loop 40 of the trigger 21. In this way the user of the tool can forwardly and rearwardly move the actuating rod 50 with respect to the extension tube 51 in which it is axially slidably guided.

The front/rear movement of the actuating rod 50 with respect to the extension tube 51 accomplishes opening and closing movement of the jaw unit 12 (FIG. 1) at the front (distal) end of the tool 10 as hereafter discussed.

To allow the jaw unit 12 to perform electrocauterization, an electrically conductive terminal pin 94 (FIG. 1) is provided on the handle unit 11 for connection to a conventional electric cauterizing current source schematically indicated at 95. More particularly, the current source 95 is connected, as indicated schematically by the dotted lines 96 and 97, respectively to the pin 94 and to the patient at the surgical site SS. As hereafter discussed, the terminal pin 94 is electrically connected to the extension tube 51 and the actuating rod 50 therein. The extension tube 51 and actuating rod 50 are of electrically conductive metal (in the preferred embodiment shown of surgical grade stainless steel.) The extension tube 51 and actuating rod 50 both are physically and electrically connected to the jaw unit 12 as hereafter more fully discussed.

The terminal pin 94 is of electrically conductive material, preferably surgical grade stainless steel. The exposed upper end of the terminal pin 94 is diametrally slotted at 100 (FIG.

2) to make it radially springy in a direction transverse to the slot 100, to enable it better to be gripped by a conventional electrical connector, not shown, connected through the line 96 to the current source 95.

Figure 2:
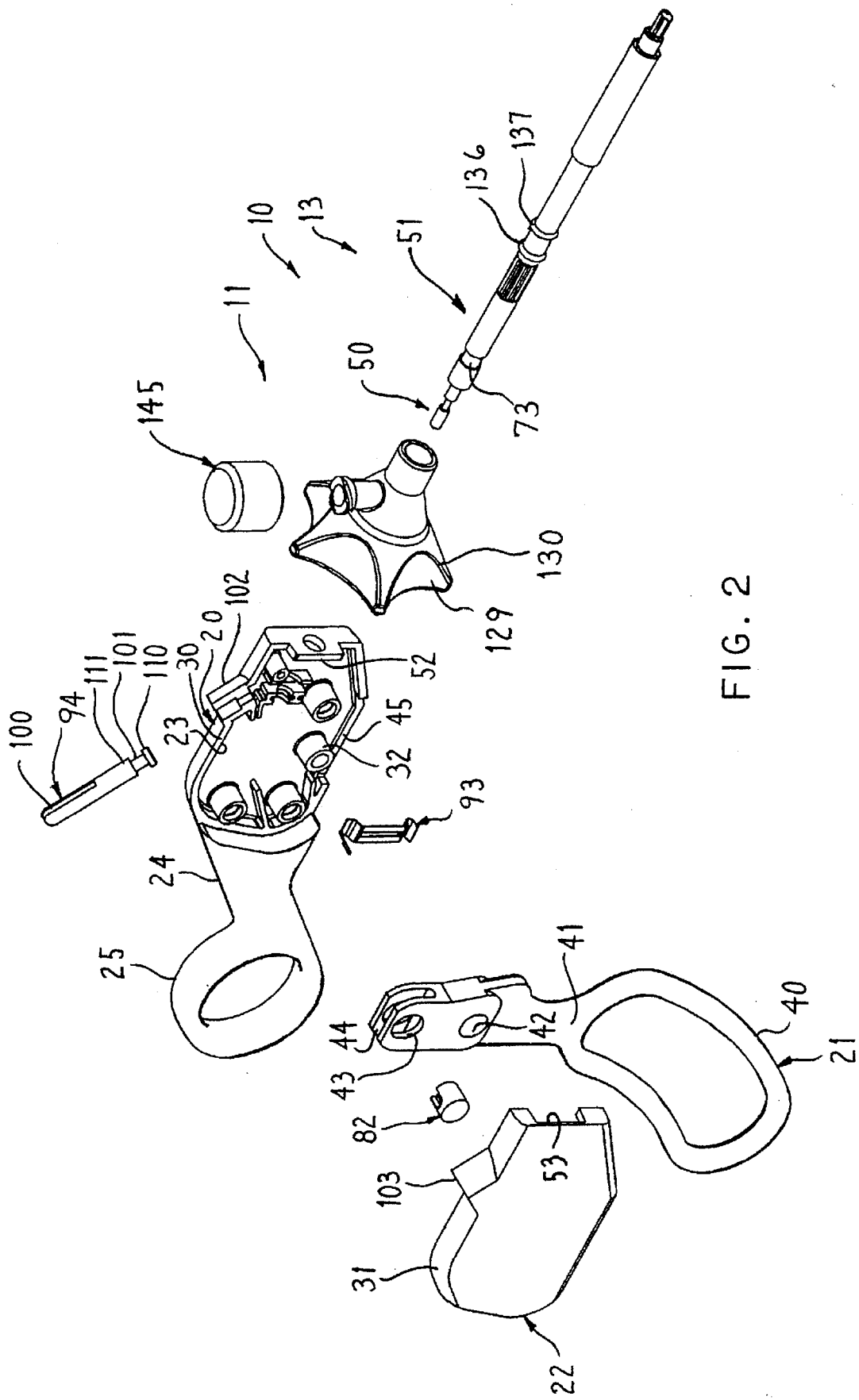
FIG. 2 is an exploded pictorial view of the proximal and mid-portions of the FIG. 1 tool.

The inner end portion of the terminal pin 94 is provided with an annular groove 101 used to fix the pin 94 in the handle unit 11. More particularly, the upper portion of the rims 30 and 31 of the body 20 and cover 22 include, preferably by integral molding therein, respective upward and rearward angled bosses 102 and 103 (FIG. 2). With the cover 22 installed along the body 20 as shown in FIG. 1, the bosses 102 and 103 abut each other to form a rearward angled composite boss 102, 103. An outwardly and rearwardly angled hole penetrates through the composite boss 102, 103 and comprises opposed grooves 104 and 105 (FIGS. 3 and 4), which define a composite hole 104, 105 communicating with the chamber 23. The outer end of the composite hole 104, 105 communicates with a radially enlarged, outwardly facing coaxial composite recess 106, 107 defined by opposed recess portions 106 and 107 respectively (FIGS. 3 and 4). In the assembled apparatus, the annular groove 101 of the pin 94 is trapped axially in the composite hole 104, 105, leaving a short inner end portion 110 of the terminal pin positively trapped inside the chamber 23 and a long outer end portion 111 of the terminal pin extending outboard of the composite recess 106, 107 and carrying outer end slot 100. In the preferred embodiment shown, the opposing recess portions 106 and 107 and the groove 104 are of circular cross section corresponding closely to that of the corresponding portions 101 and 111 of the contact pin 94. The groove 105 may be of circular cross section if desired but it can also be, as illustrated in FIG. 4, of the different cross section, here square, as desired. In any event, it is the boss portions 112 (FIGS. 3 and 4) surrounding the composite hole 104, 105, which extends radially into the annular groove 101 of the terminal pin 94 to axially trap same between the body 20 and cover 22.

The contact spring 93 (FIGS. 10 and 11) here comprises a spring tempered stainless steel sheet of uniform thickness, preferably of elongate generally rectangular shape, and having a substantially flat, elongate central portion 120 provided with an elongate rectangular central hole 121. The lower end portion 122 of the contact 93 is bent in a U-shape. The upper end portion 123 of the contact 193 is bent substantially in an L-shape. The elongate central hole 121 extends substantially the full distance between the U-shaped and L-shaped end portions 122 and 123. A tab 124 bends up from the upper left (FIGS. 7 and 11) corner of the L-shaped end portion 123.

In its installed position of FIGS. 6 and 7, the spring contact 93 abuts, with its U-shaped and L-shaped end portions 122 and 123, the interior face of the side wall 28 of the body 20 immediately below and above the saddle 90. The horns 92 of the saddle 90 protrude through the elongate hole 121 of the spring contact 93, leaving the central portion of the saddle 90 laterally outward of the flat central portion 120 of the spring contact 93. The flat central portion 120 of the spring contact 93 is spaced far enough from the body side wall 28 that the installed extension tube 51 bears forcibly against and bends slightly laterally outwardly, toward the body side wall 28, the central portion 120 of the spring contact 93, to assure firm and reliable electric current passing contact between the spring contact central portion 120 and rotatable extension tube 51. Indeed, the spring contact 93 is fixed in place on the horns 92 of the saddle 91 by the extension tube 51 pressing same laterally outward toward the side wall 28 of the body 20.

Thus installed the spring contact 93 locates its tab 124 to face upward and rearward and extend laterally inboard away from the body side wall 28. The free edge of the tab 124 resiliently presses against the interior end of the electrical terminal pin 94, so as to make firm, reliable electrically conductive contact therewith. In this matter, electric current is passed through the pin 94 and contact 93 to the periphery of the extension tube 51 and to the actuating rod 50 therein.

The outer periphery of the extension tube 51 is snugly and fixedly covered by an electrically insulated sheath 147 (FIGS. 8 and 20) which extends from within the front end of the knob 130 almost to the front end of the extension tube 51. In the preferred embodiment shown, the sheath is of conventional heat shrink tubing, for example of polytetrafluoroethylene (PTFE or Teflon brand) heat shrink tubing.

The extension tube 50, immediately ahead of the body 20 and cover 22, carries a rotator knob 130 in fixed relation thereon, so that the user, by rotating the rotator knob 130, can thereby rotate the extension tube 51 and with it, the actuating rod 50 therein. In the embodiment shown in FIG. 14, the rotator knob 130 is a rigid molded plastics element having a flat rear face whose perimeter is substantially a five pointed star, providing circumferentially spaced flute-like finger grips 129. The rotator knob 130 preferably tapers from rear to front, as shown in FIG. 1, and a rear face is provided with material saving recesses 128 (FIG. 14).

The knob 130 may be fixed to the extension tube 51 by any convenient means, but in the preferred embodiment shown such is done as follows. An axially extending keyway 131 (FIG. 8) in the rear portion of the extension tube 51 receives an axially extending key 132 fixed, preferably integrally radially, to the knob 130 and inwardly extending into the central bore 133 of the knob 130. The key 132 thus compels rotation of the extension tube 51 with the knob 130. The knob 130 is axially fixed on the extension tube 51 by any convenient means, here comprising knurling or grooving 134 on the periphery of the extension tube 51, which frictionally and or mechanically grips firmly the interior surface of the central bore 133 of the knob 130 in at least the rear portion thereof.

In the preferred embodiment shown, provision is made for transfer of liquid to or from the surgical site SS longitudinally along the annular interface between the extension tube 51 and actuating rod 50. Thus, for example, irrigation liquid may be passed to the surgical site SS or, alternatively, liquid may be suctioned from the surgical site SS. In more detail, the front portion of the central bore 133 of the knob 130 is radially enlarged, as indicated at 135 in FIG. 8, at a location immediately ahead of the grooving 134. Spaced slightly forward of the grooving 134, the exterior peripheral surface of the extension tube 51 is provided with an axially spaced pair of annular grooves to respectively receive and resilient seals, preferably O-rings, 136 and 137. Such O-rings 136 and 137 bear snugly and sealingly but rotatively on the inner surface of the enlarged front bore portion 135 of the knob 130. A radial hole 140 penetrates the perforated extension tube 51 in axially spaced relation between the O-rings 136 and 137. Radially outboard of the hole 140, the knob 130 includes a radially outwardly extending tubular stack 141 having a coaxial liquid passage 142 connectable through a liquid conduit 143 to an irrigation liquid source LS or, if desired a gravity or suction liquid drain LD as schematically indicated in FIG. 8.

The radially outer end of the stack 141 is provided with a conventional end fitting, preferably molded therein, here for example a Luer male fitting 144 suitable to fixedly and sealingly engage a conventional female Luer fitting on liquid line 143. A plug 145 may be inserted in the outer end of the stack 145 to close same when no liquid line 143 is connected thereto.

To facilitate liquid flow between the liquid hole 140 and the jaw unit 12, along the annular area between the extension tube 51 and the actuating rod 50 the corresponding length of the actuating rod 50 is provided with at least one longitudinally extending flat 146 which increases radial spacing from the interior surface of the extension tube 51 and thereby provides a longitudinal channel for liquid flow between the liquid stack 141 and the surgical site SS. In the preferred embodiment shown, the actuating rod 50 carries several (here four) evenly circumferentially spaced ones of the elongate flats 146. It is contemplated that other forms of liquid channel may be provided between the extension tube 51 and actuating rod 50, such as keyways, etc. but the flats 146 are preferred for ease in manufacture.

Attention is directed to the jaw unit 12 at the distal end of the tool 10.

The distal (rightward in FIGS. 1 and 15) end of the actuating rod 50 includes an axially deep, diametrally and forwardly opening slot 150 (FIG. 19). A diametral hole 151 (FIGS. 15, 18 and 19) extends through the actuating rod 50 immediately adjacent the distal (rightward in FIG. 15) end thereof and perpendicularly crosses the width of the slot 150. The slot 150 thus forms the distal end of the actuating rod 50 as a forward opening yoke whose arms 152 diametrally oppose each other across the forward opening slot 150.

Figure 20:
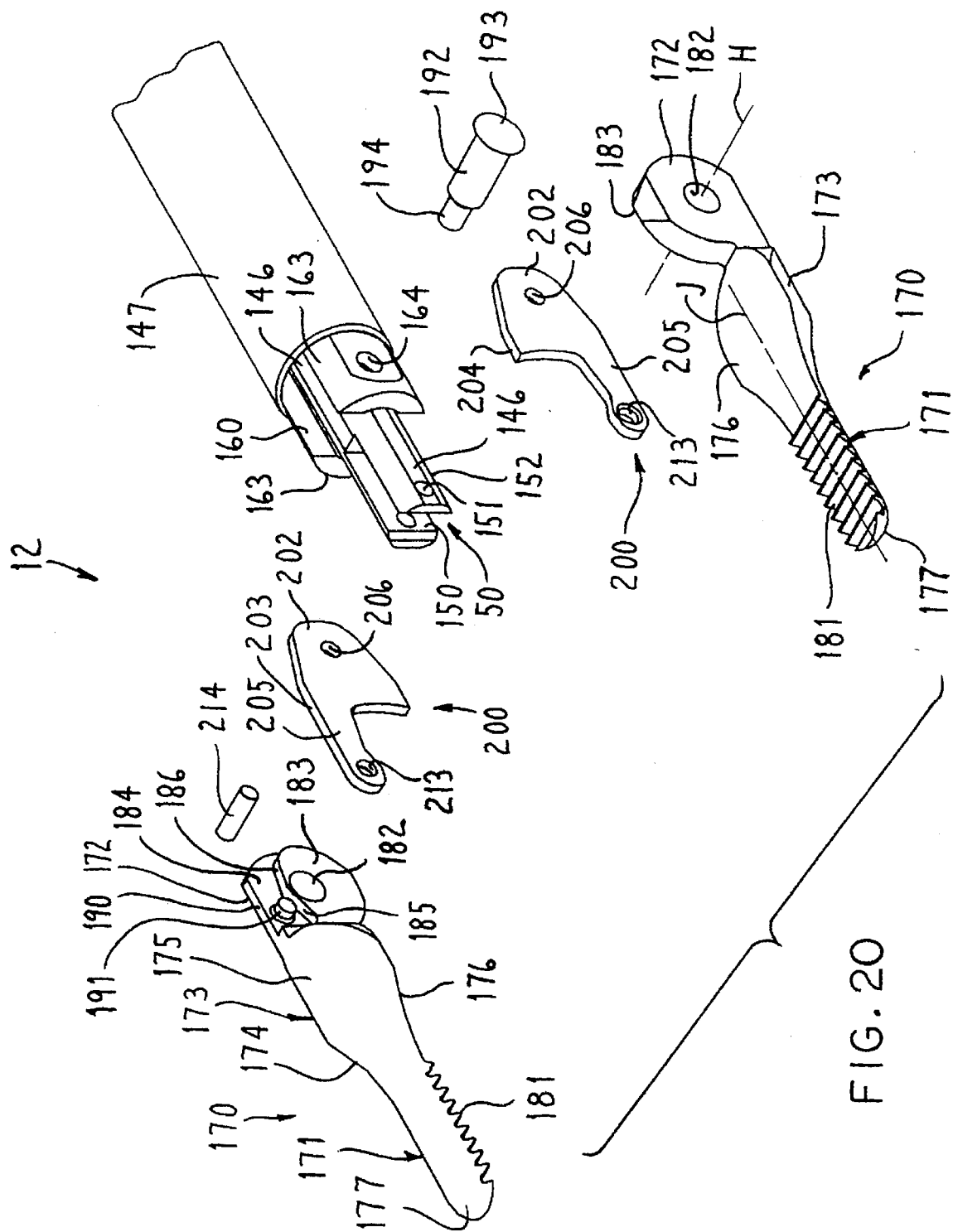
FIG. 20 is an exploded pictorial view of the jaw unit of FIG. 1.
Figure 21:
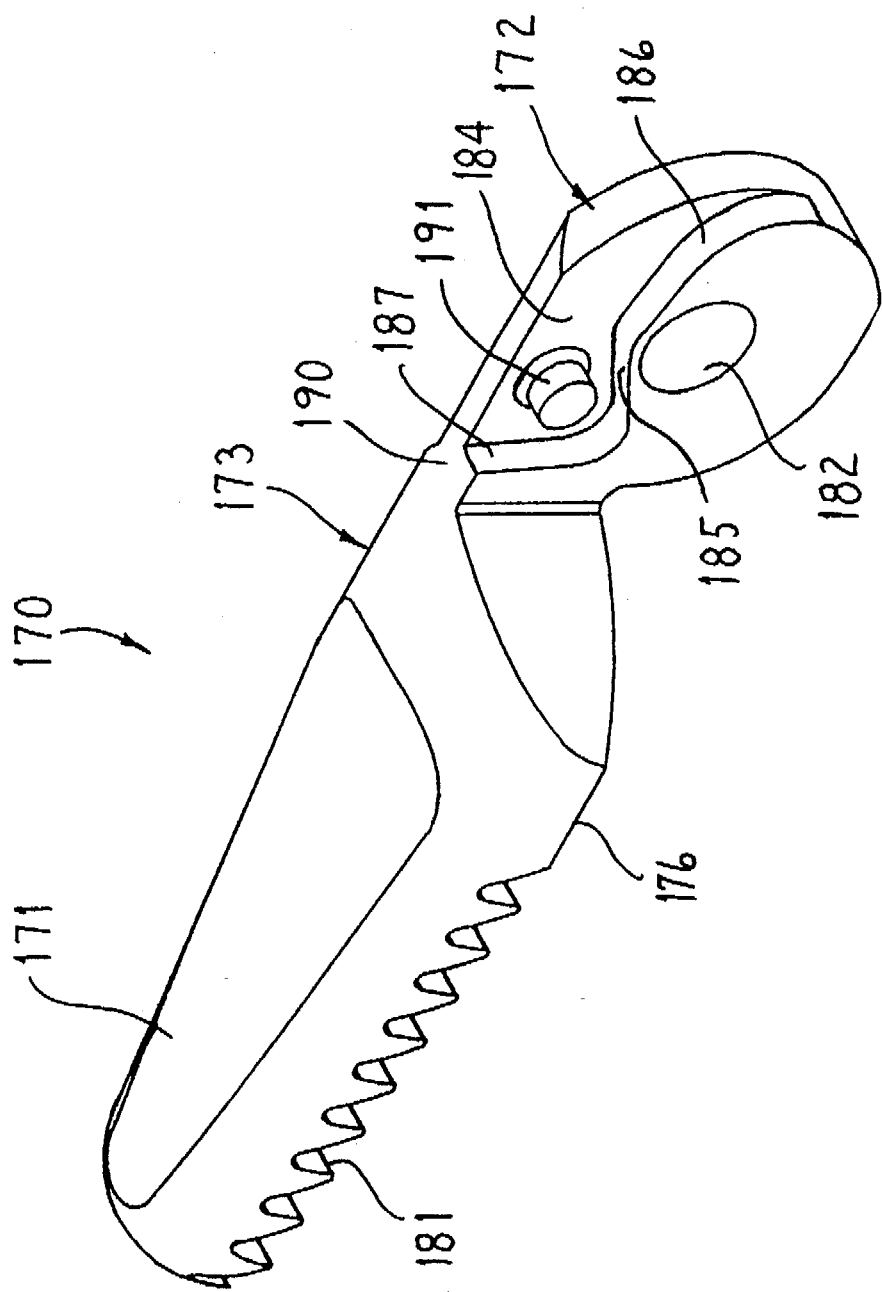
FIG. 21 is an enlarged pictorial view of a jaw of FIG. 20.

In FIG. 20, the actuating rod 20 is shown in a position during assembly of the tool 10, namely with its distal end portion extended forwardly from the extension tube 51 preparatory to its connection to the links 200 hereafter described.

The distal end of the extension tube 51 comprises a forwardly opening substantially rectangular, diametral slot 160 (FIGS. 12 and 23) of width slightly less than the inside diameter of the extension tube 51. The blind end 161 of the slot 160 is slotted to form a narrower, shorter subslot 162 (FIG. 12) of rectangular cross section and which at its forward end thus opens into the slot 160. The slot 160 and subslot 162 have the same central plane. The slot 160 and subslot 162 divide the forward end of the extension tube 51 into diametrally opposed arms 163. A diametral through hole 164 (FIGS. 12 and 20) extends through the arms 163 in a direction perpendicular to the central plane of the slot 160 and subslot 162.

The jaw unit 12 comprises a pair of preferably identical jaws 170 (FIG. 20). In the particular embodiment shown, the jaws 170 are dissector jaws having distal end portions 171 which can be brought together for gripping tissue of a patient and moved apart to release same. It is also contemplated that jaws of other types and/or purposes, for example, scissors jaws (not shown) may be substituted. The jaws 170 are preferably identical to each other, and are used with one rotated at an 180° angle about its longitudinal axis with respect to the other. The proximal end portions 172 of the jaws 170 are each of generally circular perimeter shape, as seen in FIG. 25. The mid-portion 173 of each jaw extends forward, generally tangentially, from the proximal portion 172 to the distal end portion 171. The mid-portion 173, as seen in FIG. 20, is semi-circular in cross-section. The mid-portion 173 generally tapers toward the distal end portion 171, having either a semi-cylindrical rear part 174 and tapered front part 175 as in FIG. 20 or merely tapering as in FIGS. 21–24. The mid-portions 173 of the jaws 170 have opposed flat faces 176.

Figure 22:
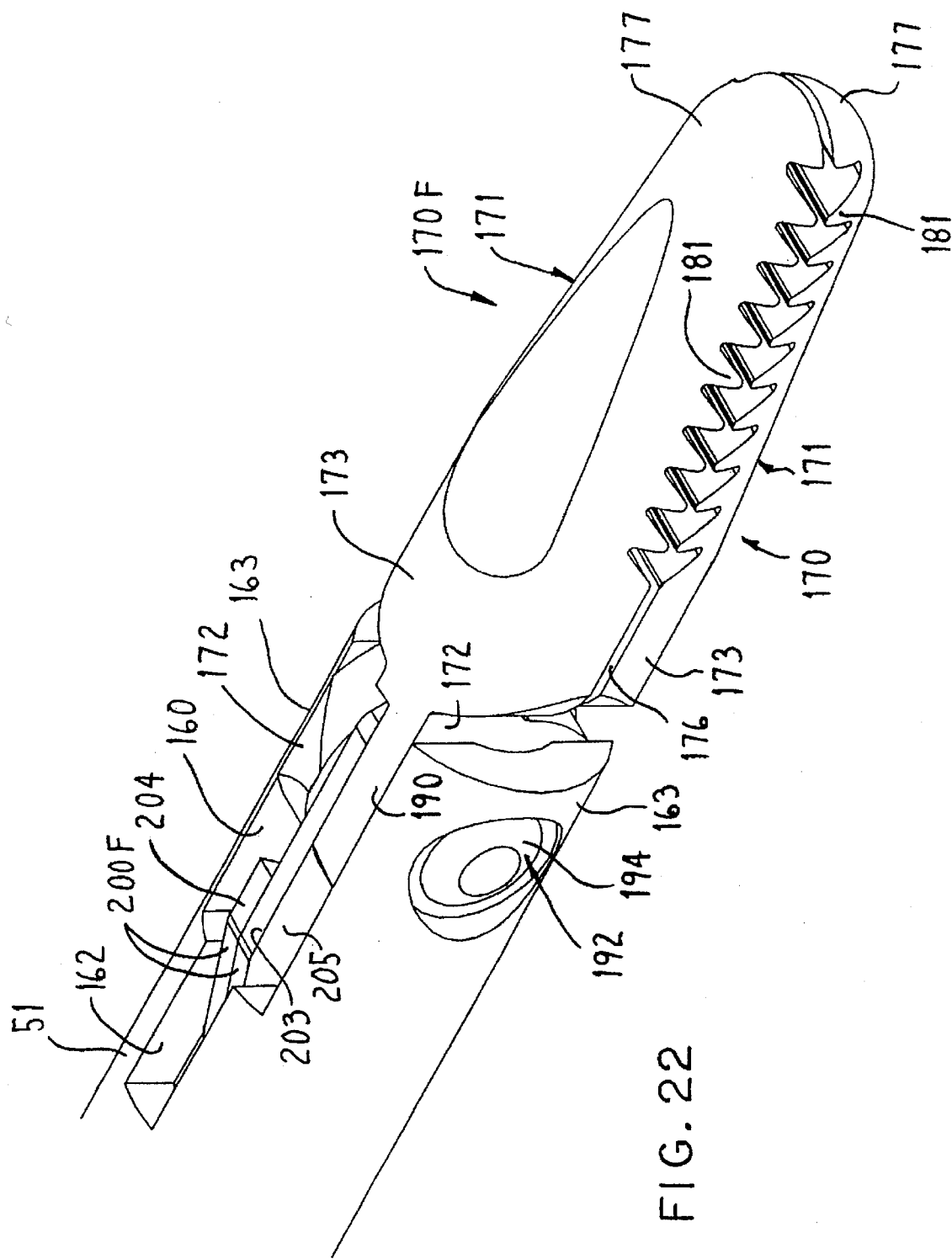
FIG. 22 is an enlarged pictorial view of the FIG. 20 jaw unit.

The distal end portions 171 of the jaws 170 are of semi-circular cross-section and forwardly extend the reduced diameter end of the mid-portion 173 and have rounded noses 177. The distal end portions 171 also continue forward the flat face 176 of the mid-portion 173, but add a forwardly extending series of transverse serrations, or teeth, 181. The teeth 181 of the jaws 170 can closely oppose each other for gripping patient tissue as generally indicated in FIG. 22. The semi-circular rounded distal end portions 171 may be substantially cylindrical as in FIG. 20 or may taper forwardly, as in FIG. 22. The proximal end portions 172 of each extend in an imaginary plane perpendicular to the plane of the flat face 176 of the corresponding jaw. The proximal portion 172 is of flat faced, hockey puck-like shape and is offset to one side of the longitudinal central axis J (FIG. 20) of the jaw 170, and more particularly of the mid-portion 173 and distal end portion 171 of the jaw. Each jaw proximal portion has a central pivot hole 182 which extends coaxially therethrough and has a central axis H which is substantially perpendicular to the longitudinal axis J of the jaw.

The opposed faces 183 of the puck-like proximal end portions 172 are relieved at 184. The relief 184 lies immediately behind the tangentially forwardly extending jaw mid-portion 173, as seen in FIG. 25. In the orientation of the jaw in FIG. 25, the relief 184 opens upward away from the pivot hole 182 and opens rearward. The bottom of the relief 184 comprises front and rear ramps 185 and 186 that rise gradually (the rear ramp 186 the more gradual of the two) to a peak close above the hole 182 to form a kind of gable roof over the hole 182. The front end of the front ramp 185 goes forward and upward to form a rear facing front wall 187 of the recess 184. The proximal and mid-portions 172 and 173 share a continuous flattened tangential edge which in the jaw orientation of FIG. 25 is substantially horizontal and at the top of the jaw.

The jaws top (in FIG. 25) edge 190, shared by the proximal and mid-portions 172 and 173, is flattened and horizontal, substantially in parallel to the longitudinal extent of the jaw 170. A pivot stub shaft 191 protrudes laterally fixedly into the recess 184.

A jaw pivot pin 192 (FIG. 20) extends through and beyond the diametral through hole 164 in the arms 163. One end 193 of the pin 192 is enlarged. The other end 194 of the pin 192 is conveniently peened over to form a further enlarged head indicated at 194 in FIG. 22. The enlarged ends 193 and 194 axially trap the pivot pin 192 in transverse spanning relation across the diametral slot 160 of the extension tube 51. The jaw pivot pin 192 extends through the pivot holes 182 in the puck-shaped proximal end portions 172 of the opposed jaws 170, which jaw end portions thus lie in parallel between the arms 163 at the distal end of the extension tube 51 and are pivotally supported on the extension tube 51 by the pivot pin 192. The jaws 170 are thus pivotable from their fully closed FIG. 22 position, through their FIG. 23 position, to their FIG. 24 90° open position. More particularly, the puck-like proximal end portions 172 of the jaws 170 are spaced side-by-side from each other in the diametral slot 160, leaving a space therebetween for links 200 discussed hereinafter.

Each jaw 170 is connected to the distal end of the actuating rod 50 (FIG. 20) by a generally P-shaped actuating link 200. Each link 200 is of flat rigid stock having a relatively large planar head 201 with a generally domed proximal end 202 and substantially parallel, forwardly extending edges 203 and 204. Each link 200 further includes a neck 205 extending forward from the head 201. The neck 205 is substantially narrower than the head 201 as measured in a direction perpendicular to the edges 203 and 204. The leg 205 continues forward the edge 203. A hole 206 is provided in the domed proximal portion 202 of the head 201.

The head 201 and arm 205 form a generally L-shaped structure, leaving a relatively large notch facing forward, and in FIG. 25 downward. Such notch is defined by an interior edge 10 extending forward along the leg 205 opposite from the edge 203, and further leaving a forward facing edge 11 which is the forward edge of the head 201. The forward end portion of the leg 205 bulges slightly into the notch at 212 to leave room for a hole 213 in the distal end portion of the leg 205 for pivotally receiving therein the pivot stub shaft 191 of the corresponding jaw 170, as seen in FIG. 25. In this way, the arm 205 of each link 201 connects pivotally to the proximal end portion 172 of the corresponding jaw in an eccentric manner, so that forward movement of the links 200 tends to close the distal portions of the jaws together, toward their FIG. 22 position, and rearward pulling of the links pivots the jaws in the opposite direction, namely toward their open FIG. 24 position.

The link 200 (FIG. 25) with its head 201 and neck 205 has a perimeter profile which may be thought to caricature, or cartoon, the head and neck of a turkey, complete with caricature beak at the join of edges 211 and 204 and caricature eye at 206.

The rear ends of the links 200 are pivotally connected by a pivot pin 214 (FIG. 20) extending through their rear pivot holes 206 and through the diametral holes 151 in the arms 152 of the actuating rod 50. In the assembled tool 10, the proximal ends 202 and pivot holes 206 of the planar head 201 of the links 200 are thus relatively pivotally retained in the forward opening slot 150 of the actuating rod 50 for pivotal motion with respect thereto and for forward and rearward movement upon corresponding forward and rearward movement of the actuating rod 50.

Successive front, mid and rear positions of the actuating rod 50 and far actuating link 200 are shown in FIG. 26 in solid line, chain line and dotted line respectively and are referenced by characters 50F, 50M and 50R, respectively and 200F, 200M and 200R, respectively. As further seen in FIG. 26, these positions of the actuating rod 50 and link 200 correspond to the respective closed, mid and open positions of the corresponding jaw 170 indicated at 170F, 170M and 170R in solid, chain and dotted lines, respectively in FIG. 26.

Just as the assembled jaws 171 are rolled 180° about their length axis with respect to each other, so to are the links 200, as generally indicated in exploded relation in FIG. 20. Thus, in use, the two necks 205 are spaced close above and below the pivot pin 192 of the jaws 171. The plate-line links 200, need to be unbendable in use, but of sufficiently small thickness to fit side-by-side in the actuating rod forward slot 150 in a freely pivotable manner, as generally shown in FIGS. 22–24.

Figure 23:
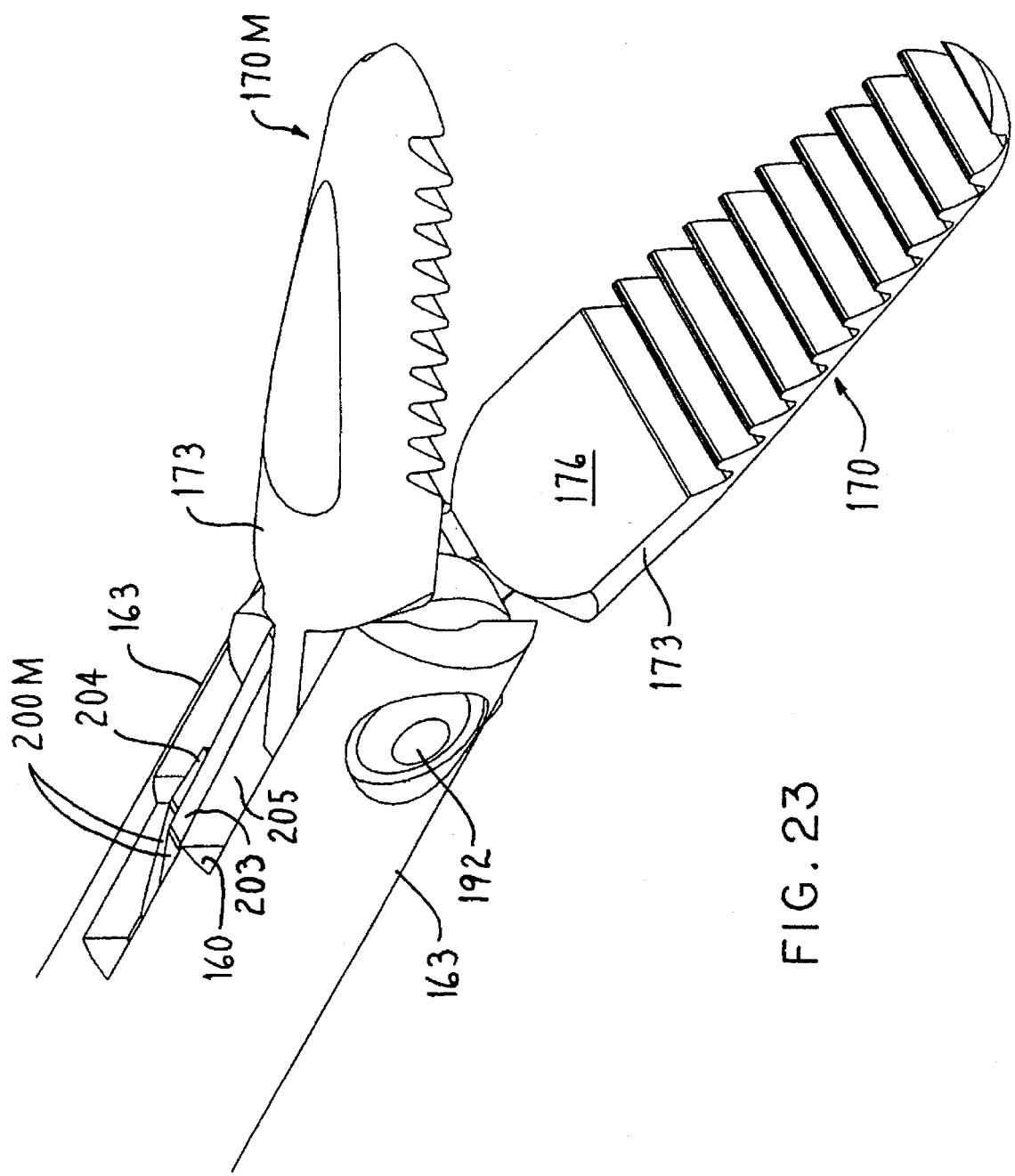
FIG. 23 is a view like FIG. 22 with the jaws partially open.
Figure 24:
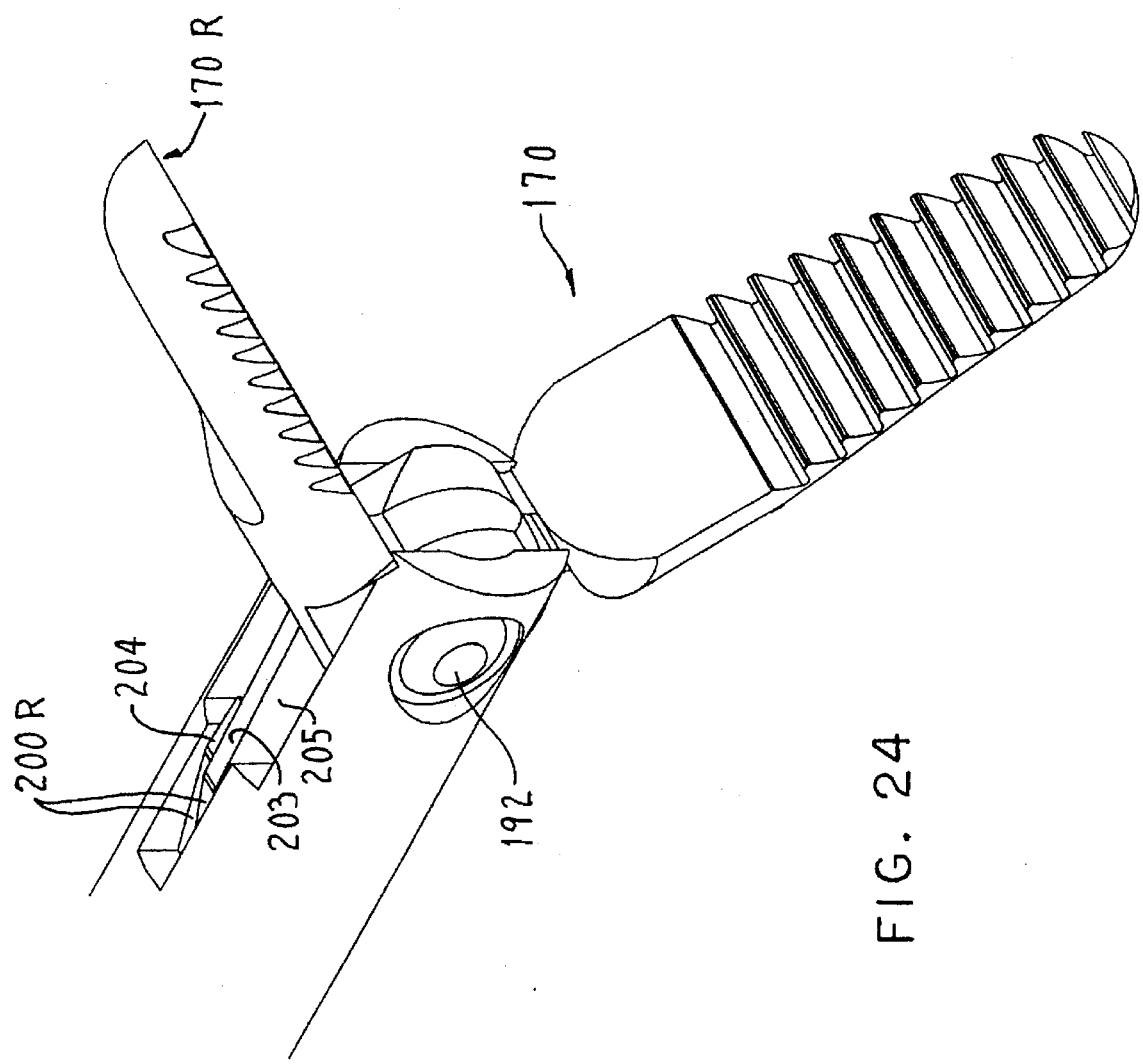
FIG. 24 is a view like FIG. 22 with the jaws fully open.

The location of the jaws 170 and links 200 with respect to the slot 160 of the extension tube 51 is seen from the top in FIG. 27, without minor visual distortions that may appear in the pictorial FIGS. 22–24.

OPERATION

The apparatus may be assembled as follows. With the links 200 assembled to the respective jaws 170, the links 200 may be inserted rearward into the forward opening slot 150 (in its exposed assembly position of FIG. 20) and pivoted there by insertion of the pin 214. The actuating rod 50, and with it the links 200 and jaws 170, may then be pulled rearward, so the links 200 and the rear portions of the jaws 170 enter the slot 160 in the front end of the extension tube 51, sufficient to allow insertion of the jaw pivot pin 192 to pivotally mount the jaws on the forward end of the extension tube 51. Thereafter, the free protruding end 194 of the pin 192 can be peened to maintain the pin 192 axially trapped on the arms 163 of the extension tube 51. The sheath 147 may be applied to the extension tube 51 either before or after installation of the jaws 170 and links 200 with respect thereto but is installed on the extension tube 51 preferably before installation of the knob 130 thereon.

With the electrically insulating sheath 147 and O-rings 136 and 137 (FIG. 8) fixed on the extension tube 51, the knob can be forced axially onto the rear end portion of the extension tube to its operative FIG. 8 position. The extension tube 51, containing the actuating rod 50, can then be inserted rearwardly through the bearing hole 54 and past the spring contact plate 93 and rear bearing part 60. With the actuating rod 50 thus pulled far enough rearward in the extension tube 51, and the upper end of the trigger 21 inserted upward through the window 45, the rear end portion of the actuating rod 50 enters the slot 44 in the top portion of the trigger and is pivotally secured in place therein by lateral insertion of the slotted drive pin 82 to operatively connect the actuating rod 50 to the trigger 21. The electrode pin 94 can then be placed laterally into the boss 102 (FIG. 7) with its inner end 110 in electrical abutting contact with the edge of the tab 124 of the contact spring 93. The cover 22 can then be fixed rim-to-rim on the body 20.

The tool 10 is operated as follows. The tool 10 is useable in laparoscopic surgery by insertion of the closed jaw unit 12 and elongate extension 13 (FIG. 1) through the usual laparoscopic cannula 14, which has previously been inserted in a conventional manner into the surgical site SS. The tool is normally handled and actuated by one hand of the user, the thumb of such hand inserted in the thumb ring 25 and one or more fingers inserted in the depending loop of the trigger 21. Pulling the bottom of the trigger 21 rearward toward the thumb loop 25 forwards the top of the trigger 21, by pivotal movement of the trigger 21 around the corresponding boss 32 (FIG. 7). The shallow arcuate movement of the top of the trigger 21, generally indicated by the adjacent arrow in FIG. 7, acts through the drive pin 82 to forward the actuating rod 50. The minor vertical component of trigger pivoting motion is absorbed by the vertical lost motion of the drive pin 82 in the oblong hole 43 in the top of the trigger and does not tend to vertically bend the rear end of the actuating rod 50, but instead applies purely axial urging thereto. Such forward movement of the actuating rod 50 moves the opposed jaws 170 to their closed position 170F (FIGS. 24 and 26). This closed position is a normal position of the jaws for insertion of the tool into the laparoscopic cannula since it minimizes the width (or diameter) of the distal portion of the tool and enables it easily to pass through the laparoscopic cannula.

Once the jaw unit 12 has been inserted through the laparoscopic cannula 14 into the surgical site SS, as shown in FIG. 1, the jaws 170 (FIGS. 22–24) can be moved from closed to open position by moving the lower part of the trigger 21 forwardly to rock the upper end of the trigger 21 rearwardly and thereby pull the actuating rod 50 rearwardly, as generally indicated in the sequence from 50F to 50R in FIG. 26. In opening the jaws 170, the legs 205 of the links 200 move rearwardly in a shallow generally horizontal arc (note the sequential positions of the pin 191 in FIG. 26). Accordingly, each rearward moving arm 205 moves radially outward slightly to clear the top of the hill formed by the saw ramps 185 and 186 (FIG. 25). As seen in FIG. 26, each arm 205 at most rises only to the outer edge of the extension tube front slot 160, so that the electrical insulating sheath 147 does not interfere with actuating motion of the links 200.

The configuration of the jaw recess 187 (FIG. 25) and corresponding link 200 represents a best compromise between desirably minimizing the outside diameter of the extension tube 51 and forwardmost extension of its surrounding electrically insulating sheath 147, with sufficient link stiffening and hence resistance to bending as to enable the link 200 to forcibly push, as well as pull, on the jaw stub shaft 191 during forcible pulling and pushing of the trigger 21. To this end, the shape and depth of the jaw recess 184 is selected to allow maximum width of the link neck 205, particularly to maximize the amount of link neck material surrounding the pivot pin 191 and to maximize the width of the link neck 205 where it merges into the link head 201. The substantial width of the link head 201 at its forward end portion, from which the neck 205 forwardly extends, permits maximizing of spacing between the parallel, forward extending edges 203 and 204 of the head 201 to allow them to lie closely to the surrounding sheath. This configuration also allows the forward portion of the link head 201 adjacent the neck 205 to lie close behind the puck-shaped jaw portion 172 in the forward position of the link 200. Maximizing the width of the link head 201 roughly halfway between the pivot holes 206 and 205 thereof, by maximizing the widthwise spacing of the link head edges 203 and 204, advantageously allows each link head 201 in this area between edges 203 and 204 to reinforce the other link 200 against any tendency to twist between its front and rear ends, particularly when the links 200 are pushing the jaws 170 closed, to grip forcibly-a portion of patient tissue. Also, the configuration of the link 200 and the attached rear portion of the jaw 170 advantageously allows the user to open the dissector jaws very widely and yet be capable of easily and carefully controlling the relative position of the jaws.

The plate-like links 200 (FIGS. 22–24 and 26) must be very thin to pivotally fit side-by-side with each other between the puck-like proximal end portions 172 of the jaws 170 in the extension tube forward slot 160, in view of the small outside diameter extension tube 51 required to slidably insert in a conventional laparoscopic surgical cannula 14 (FIG. 1). For example, in one unit constructed according to the invention, the height (vertically in FIGS. 20 and 27) of the puck-like jaw proximal end portion 172 was about 0.186 inch, the outside diameter of the extension tube 51 was about 0.188 inch, and the width of its front slot 160 was about 0.095 inch (less than 1/10 inch). In the same unit, the thickness of each puck-like jaw proximal end portion 172 was about 0.45 inch and the thickness of the recess 184 therein was sufficient to accommodate a link 200 of about 0.018 inch thick. This left about 0.001 inch clearance at the sliding interfaces between the extension tube 51 (at the forward slot 160 thereof), the jaw proximal end portions 172 and the links 200. Though of relatively stiff material (preferably surgical grade stainless steel), nevertheless a link 200, and particularly a link neck 205, only 0.018 inch thick (approximately the combined thickness of pages 1–5 of the present specification) would be expected to bend responsive to a relatively small lengthwise compressive force thereto, with the link unsupported. In the same unit built according to the invention, the minimum width of the link neck 205 was about 0.047 inch (approximately 3/64 inch, about the maximum allowed by the space between the pivot pin 192 and the sheath 147). On the other hand, the width between the flat edges 203 and 204 of the link head 201, which head is spaced from and does not need to clear the pin 192, was about 0.175 inch (a bit over 11/64 inch), to maximize the stiffness of the head 201 in response to axial compressive forces on the link 200.

With these very thin links 200 (i.e., 0.018 inch in such one unit constructed according to the invention), sufficient link stiffness and resistance to bending (as to enable the link 200 to forcibly push on the jaw stub shaft 191 sufficient to press the jaws 170 to forcibly grip a portion of patient tissue) is here achieved by close lateral support of the link by laterally adjacent structure. More particularly, the narrow neck 205 of each link is closely laterally slidably backed on one side by the side of the recess 184 in the corresponding jaw 170, which jaw 170 is in turn laterally backed by the extension tube 51 at the edge of the slot 160. The link narrow neck 205 is laterally supported on the other side by the proximal portion 172 of the other jaw 170, diametrally remote from the recess 184 therein, which other jaw rear end portion is in turn laterally backed by the material of extension tube 51 at the other side of the slot 160 therein. As seen in FIG. 26, most of the narrow link neck 205 is continuously closely sandwiched in slidable but laterally supported relation between the laterally imposed jaw rear end portions. Further, the length portion of the neck 205 laterally supported between proximal end portions of adjacent jaws 170 is maximized with the jaws closed or almost closed, as in tissue grasping relation, and is only lessened with the jaws pulled apart. Thus as maximum gripping force is applied to the jaws by forward pushing on the actuating rod 50, the jaw necks 205 are in their range of maximum lateral support between the cheeks of the adjacent jaw rear end portions. Also, the narrowed rear end portions 202 of the links 200 are closely laterally supported by the lateral edges of the reduced width subslot 162 of the extension tube 51. The widest portion of the link 200, between the parallel top and bottom edges 203 and 204 in FIG. 25, while not laterally supported by the jaws 170 or extension tube 51, nevertheless resists bending upon axial compression of the link due to its short axial length, its maximized lateral (vertically in FIG. 25) width and the close side-by-side mutual support against bending one toward the other achievement of the cheek-to-cheek sliding abutment of these two portions of links 200. The result is that the links 200 are capable of transmitting substantially higher axially compressive forces than would have otherwise been expected.

The very small clearances laterally between the extension tube slot edges, jaw proximal end portions and link necks maximizes the lateral support and hence resistance to bending imparted to the link necks by the sandwiching jaw rear end portions and extension tube slot edges. Slight interference to sliding between the parts is tolerable since it adds to the resistance to bending of the link necks. In a figurative sense, the link necks almost become an interior part of a solid block although one in which they are allowed to translate and pivot in their own plane. In some instances, it may be desirable during surgery to pass an electric cauterizing current through the jaws 170 to patient tissue, for cauterizing same. This may be true in the case of dissector type jaws as well as with jaws of other types, such as conventional jaws (not shown) capable of scissors-like cutting. To that end, the electric cauterizing current source 95 can in a conventional manner be connected by electric conductors 96 and 97 (FIG. 1) to the terminal pin 94 at the proximal portion of the tool 10, as well as to the patient near the surgical site SS. Cauterizing current is conducted by the spring-like contact 93 from the inner end 110 of the electric terminal pin 94 to the extension tube 51. Such electrical contact is particularly reliable due to bearing of the spring contact edge 124 forcibly and resiliently against the inner end portion 110 of the pin 94 and due to the resilient self-urging of the mid-portion of the springy contact member 93 radially against the periphery of the extension tube 51, such contact being continuous despite possible rotation of the extension tube 51 by user rotation of the knob 130. Thus, electric current is supplied to the extension tube 51 as well as to the actuating rod 51 electrically contacting the interior thereof, through the pivot pins 192 and 214 (FIG. 20) of shafts 191 and links 200 to the jaws 170, all of which are of electrically conductive material, preferably surgical grade stainless steel.

As mentioned, liquid flow is permitted between the surgical site SS and the stack 141 on the rotate knob 130. Thus, for example, during a surgical procedure, irrigation liquid from a liquid source LS (FIG. 8) can be admitted to the stack 141 on the rotate knob 130 to thus feed through the hole 140 and along the flats 146 on the actuating rod 50 (and thus within the extension tube 51) to enter the surgical site SS adjacent the jaws 170.

It will be noted that the tool 10 can be manufactured inexpensively, the parts being of molded plastics material in the handle unit 11, and so can be sold and used as a disposable, for disposal after a surgical procedure on a single patient, thereby avoiding the expense of and risks associated with resterilization.

The human hand is formed such that it can apply more force to the finger loop of the trigger 21 in pulling it rearwardly toward the thumb ring (by clenching the hand into a fist) than by pushing the finger loop of the trigger forwardly. In consequence, the closing force applied to the jaws and hence their gripping force on patient tissue is maximized at least in part due to the arrangement of the links 200 to close the jaws 170 in response to such a fist clenching, rearward pull on the lower portion of the trigger 21.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A laparoscopic surgical tool, comprising:
   a proximal handle unit;
   a distal jaw unit comprising a pair of opposing relatively pivotable jaws and means for applying electrocautery current to said jaw unit;
   an intermediate extension unit for operatively connecting said handle unit to said distal jaw unit for actuating said distal jaw unit upon manipulation of said proximal handle unit;
   means associated with said intermediate extension unit for flowing liquid therealong between said proximal handle unit and said distal jaw unit, said intermediate extension unit including an elongate extension tube and an elongate actuating rod axially reciprocably housed in said extension tube, said extension tube and actuating rod extending between and being operatively connected to said proximal handle unit and distal jaw unit for actuating the latter upon user manipulation of the former, said means for flowing liquid comprising a hole radially through said extension tube near said proximal handle unit and opening to said actuating rod, said actuating rod having a surface relief extending from said hole in said extension tube forwardly to a distal end of said actuating rod and opening to a surgical site in which said distal jaw unit has been inserted.

2. The apparatus of claim 1 in which said surface relief comprises a flat on the periphery of the actuating rod opposing a concavely rounded interior surface of the surrounding extension tube and therewith defining an axial liquid passage between said extension tube hole and said distal jaw unit.

3. A laparoscopic surgical tool, comprising:
   a proximal handle unit;
   a distal jaw unit including opposed relatively pivotable jaws;
   an intermediate extension unit operatively connecting said proximal handle unit for actuating said distal jaw unit in response to manual actuation of said proximal handle unit, said intermediate extension unit comprising an extension tube and an actuating rod reciprocable longitudinally in said extension tube, at least one of said extension tube and actuating rod being electrically connected to said jaws, said extension tube and actuating rod being of electrically conductive material for applying electric current to said jaws for carrying out cauterization of patient tissue by said jaws, said extension tube having an outside and an inside, a conductive spring having a first portion backed by said proximal handle unit and a second portion resiliently pushing against said outside of said extension tube for applying electric current thereto, said spring having a third portion, an electrically conductive terminal element having an interior end portion resiliently forcibly engaged by said spring third portion for flowing electric current thereto and having an exterior portion connectable to a conventional electrical source, said proximal handle unit comprising a housing wall through which said terminal element extends, a saddle protruding from said wall into the interior of said proximal handle unit, said extension tube extending across said saddle, said spring comprising a leaf having a substantially flat central portion having an elongate slot therethrough, said saddle having horns at opposite ends thereof extending through end portions of said slot to locate said spring tangentially of said extension tube, said spring having ends backed by said wall and pushing said slotted central portion of said spring resiliently against said extension tube to maintain firm electrical contact against said extension tube despite rotation of said extension tube and jaw unit with respect to said proximal handle unit.

4. A laparoscopic surgical tool, comprising:
   a proximal handle unit;
   a distal jaw unit comprising first and second jaws and means for applying electrocautery current to said distal jaw unit, said first jaw being movable with respect to said second jaw;
   an intermediate extension unit operatively connecting said proximal handle unit and distal jaw unit for actuating said distal jaw unit in response to manual actuation of said proximal handle unit, said intermediate extension unit comprising an elongate extension tube mounted for rotation on said proximal handle unit, a finger actuable rotor fixed on said extension tube adjacent said proximal handle unit for actuation by the finger of a user handling the proximal handle unit, said extension tube having an outside and an interior, said intermediate extension unit further including an actuating rod axially reciprocable in said extension tube, said extension tube and actuating rod both engaging portions of said distal jaw unit for actuation of the latter, a liquid port in said rotor extending radially therethrough to said extension tube, said extension tube having a radial hole open to said liquid port, annular seals axially flanking said liquid port and radial hole and radially sealingly interposed between said rotor and extension tube for preventing liquid leakage therebeyond along said outside of said extension tube, said actuating rod being relieved axially from said radial hole and in liquid communication therewith to the distal jaw unit for passing liquid between said port and said distal jaw unit radially between said actuating rod and said interior of said extension tube.

5. The apparatus of claim 4 in which said proximal handle unit has electrically insulated external parts, said rotor being of electrically insulating material, said extension tube being covered by an insulative sheath contiguous with said rotor and extending generally adjacent the distal jaw unit for guarding the user of the tool against accidental contact with electric current carrying parts of the apparatus, said extension tube being of electrically conductive material for connection near a proximal end of said tool to a conventional electric cauterizing current source.

6. A laparoscopic surgical tool comprising:
a proximal handle unit;
a distal jaw unit engagable with a patient for engaging patient tissue at a surgical site and means for applying electrocautery current to said jaw unit;
an intermediate extension unit for actuating said distal jaw unit in response to manual actuation of said proximal handle unit, said intermediate extension unit comprising an elongate actuating rod supported for reciprocation with respect to said proximal handle unit and distal jaw unit for actuating said distal jaw unit, said actuating rod having an annular groove adjacent its proximal end defining a grooved portion of said actuating rod, said proximal handle unit comprising a housing in which said proximal end of said actuating rod extends, said proximal handle unit also having a trigger actuable by a user and extending into said housing, an interior end of said trigger having an end opening notch into which said proximal end of said actuating rod extends, said trigger having a through hole spanning said notch and said grooved portion of said actuating rod, said through hole and actuating rod having axes which cross substantially perpendicularly, a cylindrical plug-like member extending through said through hole in said trigger, said plug-like member having an end opening notch diametrally therethrough, said grooved portion of said actuating rod being received in said notch in said cylindrical plug-like member, said plug-like member being radially snugly held in said through hole against movement with respect to said trigger in a direction substantially axially of said actuating rod but being radially loosely held in said through hole in said trigger in a direction generally parallel to the length direction of said trigger, said trigger being pivotally mounted on said housing at a location spaced from the ends of said trigger, such that manual pulling of said trigger proximally results in distal movement of said actuating rod along the length axis of said actuating rod.

7. The apparatus of claim 6 in which said housing has opposed side walls which closely sandwich said trigger and said plug-like member to prevent escape of said plug-like member from said through hole and so as to thereby maintain reciprocating connection of said trigger to said actuating rod.

8. The apparatus of claim 7 in which said intermediate extension unit further includes an extension tube in which said actuating rod is axially reciprocable, and including a bearing saddle on at least one of said side walls and protruding inward therefrom and snugly but rotatably supporting said extension tube with respect to said housing, said extension tube having an annular groove engaging said saddle to prevent axial motion of said extension tube with respect to said housing.

9. The apparatus of claim 8 in which a generally T-shaped protrusion on the opposite housing side wall prevents escape of said extension tube radially out of said bearing saddle.

10. The apparatus of claim 9 including a further saddle fixed in said housing between said bearing saddle and a forward end of said housing and loosely radially opposing said extension tube, and an electrically conductive spring located by the last mentioned said saddle and pressed tangentially against said extension tube for imparting electric current thereto, said extension tube being of electrically conductive material for applying electric cauterizing current to said distal jaw unit, said spring being backed by the adjacent side wall of said housing.

11. The apparatus of claim 8 in which said housing has a front wall and the through hole therein through which said extension tube extends forwardly from within said housing towards said distal jaw unit, said hole being spaced axially in front of said bearing saddle for supporting of said extension tube for rotation at two axially spaced locations thereon with respect to said housing.

12. A laparoscopic surgical tool of twin jaw type, comprising:
a proximal handle unit;
a distal jaw unit incorporating jaws relatively movable in respect to each other and means for applying electrocautery current to said jaw unit;
an intermediate extension unit for mounting said distal jaw unit on said proximal handle unit and for actuation of said distal jaw unit by said proximal handle unit, said jaws having laterally snugly abutting rear end portions, said intermediate extension unit comprising an elongate extension tube and an actuating rod reciprocable within said extension tube in response to actuation of said proximal handle unit to move jaws of said distal jaw unit, said distal jaw unit further including a pair of plate-like links, said jaws of said distal jaw unit being pivotally mounted on a distal end portion of said extension tube, said links being pivotally secured at rear end portions thereof to said actuating rod and at front end portions thereof to said rear end portions of said jaws, said rear end portions of said jaws having laterally opposed relief spaces, the front end portions of said links being disposed in said relief spaces, said jaw rear end portions snugly laterally sandwiching and supporting said front end portions of said plate-like links, said extension tube having a front end portion having a slot forwardly opening therefrom and leaving laterally spaced forward extension walls for snugly sandwiching said rear end portions of said jaws therebetween, whereby the front end portions of said links are supported laterally against lateral bending by flanking portions of the rear end portions of said jaws, despite axial compressive forces on said links for closing said jaws into gripping relation with patient tissue.

13. The apparatus of claim 12 in which a forward portion of said extension tube has a subslot extending rearward therein from said forwardly opening slot, the rear end portions of said links being snugly received in said subslot and being snugly laterally supported by portions of said actuating rod laterally bounding said subslot so as to help resist bending of said rear end portions of said links in response to axial compression forces thereon for closing said jaws to grip patient tissue, a forward end portion of said links being pivotally fixed to said jaw rear end portions, pivot means for pivotally supporting said jaw rear end portions on said extension tube front end portion, the front end portions of said links extending forwardly eccentrically of said pivot means, such that the front end portions of said links have maximum length sandwiched between said jaw rear end portions as the jaws move to their closed position on patient tissue.

14. The apparatus of claim 13 in which each link has a generally P-shaped profile said link having a maximum width intermediate at the ends thereof, a reduced width at a rearward end portion thereof laterally supported by the sides of said subslot, the front end portion of said link being of minimum width, so as to clear said pivot means of said jaw rear end portions.

15. The apparatus of claim 12 in which the relief space in each jaw rear end portion has a hill to radially accommodate a central pivot pin defining means for pivotally mounting said jaws on said extension tube, said link front end portion being narrowed in opposition to said hill to clear same, said jaws being substantially identical to each other but rotated about 180° with respect to each other so that the relief space in one jaw is closed by an unrelieved portion of the opposed face of the rear end portion of the other jaw, said link having a front end pivotally fixed to a pivot element in a front end portion of said relief space, each link front end portion being snugly laterally sandwiched between a side wall of the relief space in its corresponding jaw rear end portion and the unrelieved portion of the opposing face of the other jaw rear end portion to support said link front end portion against bending during compression thereof to forcibly close the jaws on patient tissue.

16. The apparatus of claim 15 in which the rear end portion of each jaw is of generally hockey puck-like shape with said relief space being in one end face thereof and having a convexly rounded rear facing perimeter portion, a forward portion of said extension tube has a subslot extending rearward therein from said forwardly extending slot, an intermediate portion of said link being widened to closely follow with its width the rear perimeter shape of said jaw rear end portion, such that said link is of maximum width in a relatively axially narrow central portion unsupported laterally by either the adjacent jaw rear end portions or the subslot in the extension tube.

17. The apparatus of claim 12 in which said jaws are substantially identical to each other but rotated 180° about their length axis with respect to each other, each jaw rear end portion having a circumferentially rounded substantially flat sided disk-like shape and a tissue gripping portion extending forward therefrom, said tissue gripping portions each having a forward extending surface to oppose the corresponding forward extending surface of the other jaw in tissue gripping relation, said forward extending tissue gripping surfaces being closeable together substantially along a tissue gripping plane, said disk-like rear end portions of said jaws being opposed laterally in close side-to-side relation across an abutment plane and having a common central bore for receiving a pivot pin supported on opposite sides of said slot in said front end portion of said extension tube, the length axis of said pivot pin being substantially in said tissue gripping plane of said jaws, said forward extending tissue gripping portions of said jaws having rear parts each substantially of lateral width twice the lateral thickness of said disk-like rear end portions, said forward extending tissue gripping portions of said jaws bisected by said abutment plane of said disk-like jaw rear end portions.

* * * * *